(12) United States Patent
Bortlein et al.

(10) Patent No.: US 10,470,884 B2
(45) Date of Patent: Nov. 12, 2019

(54) TREATMENT CATHETER MEMBER WITH ENCIRCLING FUNCTION

(71) Applicant: HIGHLIFE SAS, Paris (FR)

(72) Inventors: Georg Bortlein, Paris (FR); Malek Nasr, Paris (FR)

(73) Assignee: HIGHLIFE SAS, Paris (FR)

( * ) Notice: Subject to any disclaimer, the term of this patent is extended or adjusted under 35 U.S.C. 154(b) by 281 days.

(21) Appl. No.: 15/448,020

(22) Filed: Mar. 2, 2017

(65) Prior Publication Data
US 2017/0172554 A1 Jun. 22, 2017

Related U.S. Application Data

(62) Division of application No. 14/383,614, filed as application No. PCT/EP2013/054442 on Mar. 5, 2013, now Pat. No. 9,770,332.
(Continued)

(30) Foreign Application Priority Data

Mar. 6, 2012 (DE) .................. 10 2012 101 877

(51) Int. Cl.
*A61B 17/00* (2006.01)
*A61F 2/24* (2006.01)
(Continued)

(52) U.S. Cl.
CPC ...... *A61F 2/2466* (2013.01); *A61B 17/00234* (2013.01); *A61F 2/2427* (2013.01);
(Continued)

(58) Field of Classification Search
CPC .... A61F 2/2418; A61F 2/2466; A61F 2/2409; A61F 2/2427; A61F 2/243; A61F 2/2436; A61F 2/2439; A61B 17/00234
See application file for complete search history.

(56) References Cited

U.S. PATENT DOCUMENTS

| 7,959,666 B2 | 6/2011 | Salahieh et al. |
| 2002/0013571 A1 | 1/2002 | Goldfarb et al. |

(Continued)

FOREIGN PATENT DOCUMENTS

| WO | 2009/155561 A2 | 12/2009 |
| WO | 2011011138 A2 | 1/2011 |

(Continued)

OTHER PUBLICATIONS

Sep. 19, 2016 Office Action Issued in U.S Appl. No. 14/383,614.
(Continued)

*Primary Examiner* — Tuan V Nguyen
(74) *Attorney, Agent, or Firm* — Oliff PLC

(57) ABSTRACT

A catheter member for interacting with a circumferential tissue structure includes: an elongate primary catheter having at least one inner lumen and extending along a longitudinal axis; first and second elongate secondary catheters, each having an inner lumen, and each positionable in an inner lumen of the primary catheter to be moveable relatively thereto and exposable therefrom; and a first flexing mechanism to provide a distal end portion of the first and/or second secondary catheter with a tendency to assume a first secondary bent shape. The distal end portion of the first and/or second secondary catheters is provided so as to be able to be flexed by the first flexing mechanism to form an arm portion substantially transverse to the direction of the longitudinal axis of the primary catheter so as to assume the first secondary bent shape when exposed from a distal end portion of the primary catheter.

24 Claims, 31 Drawing Sheets

Related U.S. Application Data

(60) Provisional application No. 61/607,073, filed on Mar. 6, 2012.

(51) Int. Cl.
*A61B 17/04* (2006.01)
*A61B 17/221* (2006.01)

(52) U.S. Cl.
CPC .......... *A61F 2/2451* (2013.01); *A61F 2/2457* (2013.01); *A61B 2017/00243* (2013.01); *A61B 2017/00331* (2013.01); *A61B 2017/00358* (2013.01); *A61B 2017/00783* (2013.01); *A61B 2017/00845* (2013.01); *A61B 2017/00867* (2013.01); *A61B 2017/00871* (2013.01); *A61B 2017/00876* (2013.01); *A61B 2017/0472* (2013.01); *A61B 2017/2212* (2013.01)

(56) References Cited

U.S. PATENT DOCUMENTS

| | | |
|---|---|---|
| 2004/0039442 A1 | 2/2004 | St. Goar et al. |
| 2004/0127982 A1 | 7/2004 | Machold et al. |
| 2004/0243230 A1 | 12/2004 | Navia et al. |
| 2005/0143809 A1 | 6/2005 | Salahieh et al. |
| 2007/0038293 A1 | 2/2007 | St. Goar et al. |
| 2008/0228267 A1* | 9/2008 | Spence .............. A61B 17/0401 623/2.36 |
| 2009/0319037 A1 | 12/2009 | Rowe et al. |
| 2011/0218620 A1 | 9/2011 | Meiri et al. |
| 2011/0224607 A1 | 9/2011 | Vogelbaum et al. |
| 2013/0211513 A1* | 8/2013 | Rourke ................. A61F 2/2466 623/2.37 |

FOREIGN PATENT DOCUMENTS

| | | |
|---|---|---|
| WO | 2011/137531 A1 | 11/2011 |
| WO | 2012/004679 A2 | 1/2012 |

OTHER PUBLICATIONS

Jul. 25, 2013 International Search Report issued in International Application No. PCT/EP2013/054442.

Jul. 25, 2013 Written Opinion issued in International Application No. PCT/EP2013/054442.

* cited by examiner

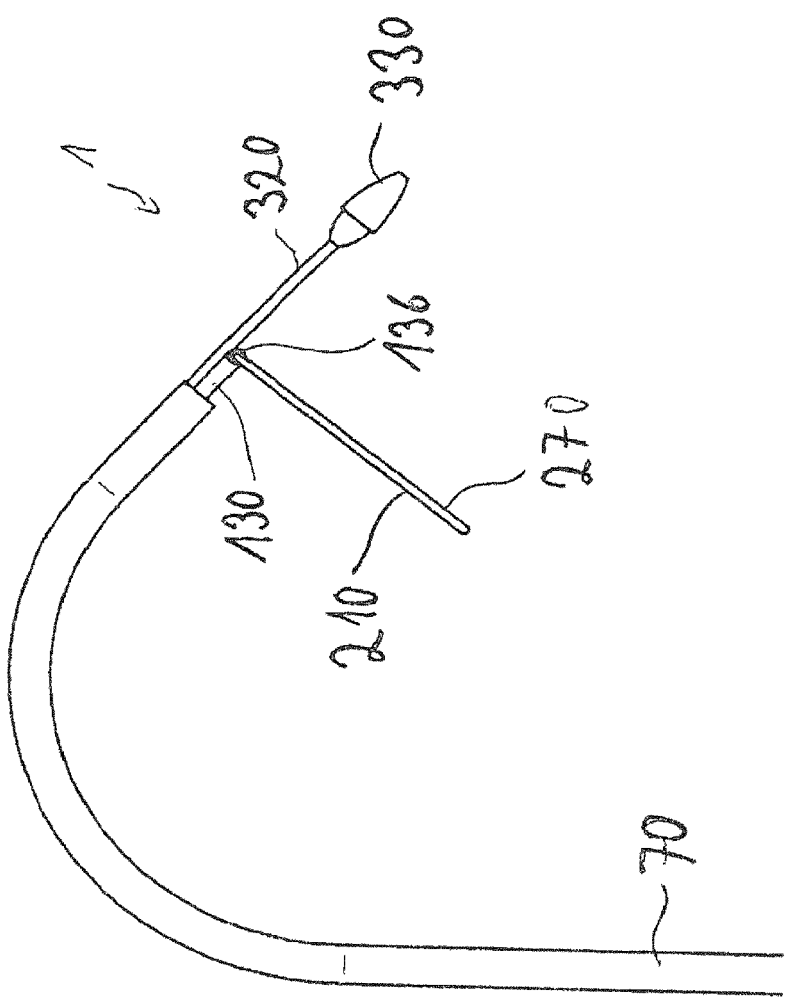

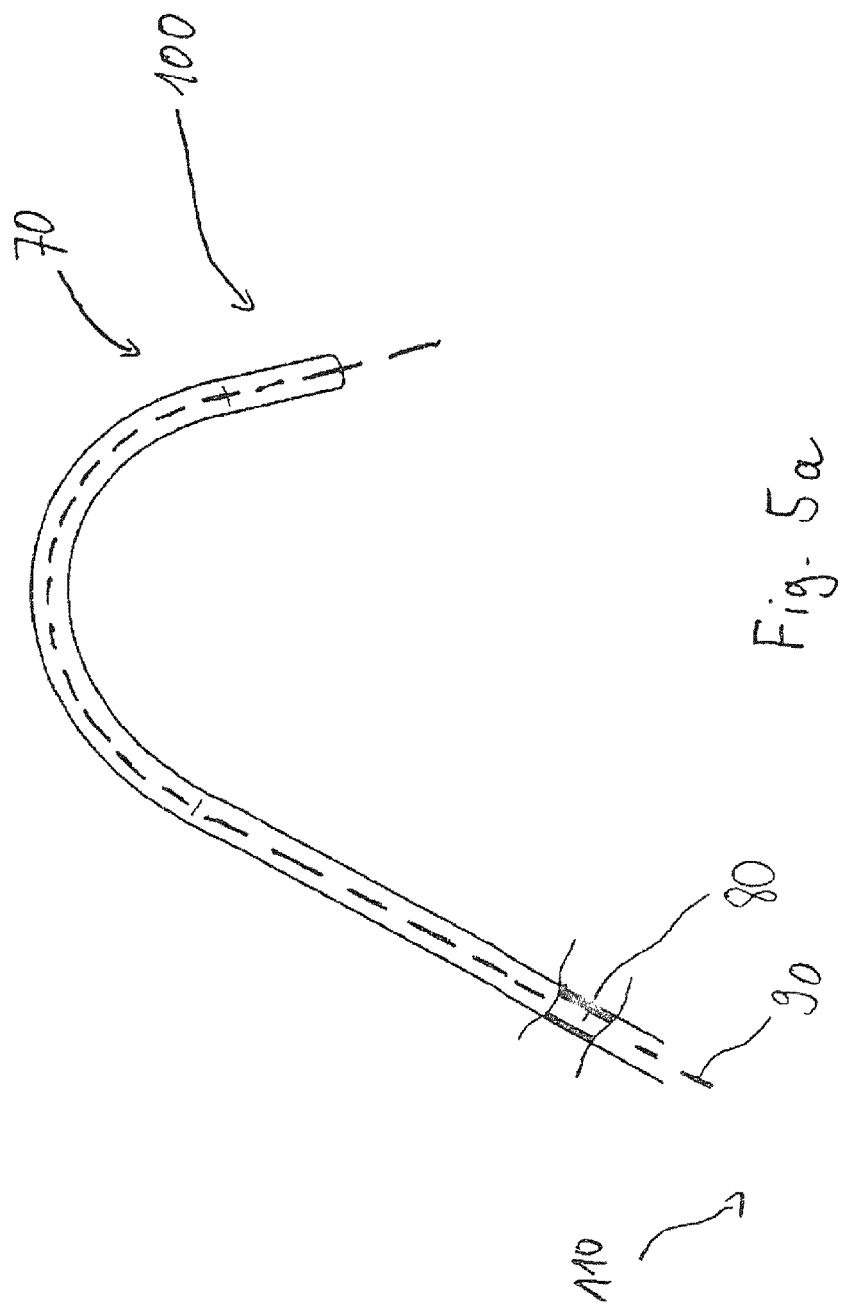

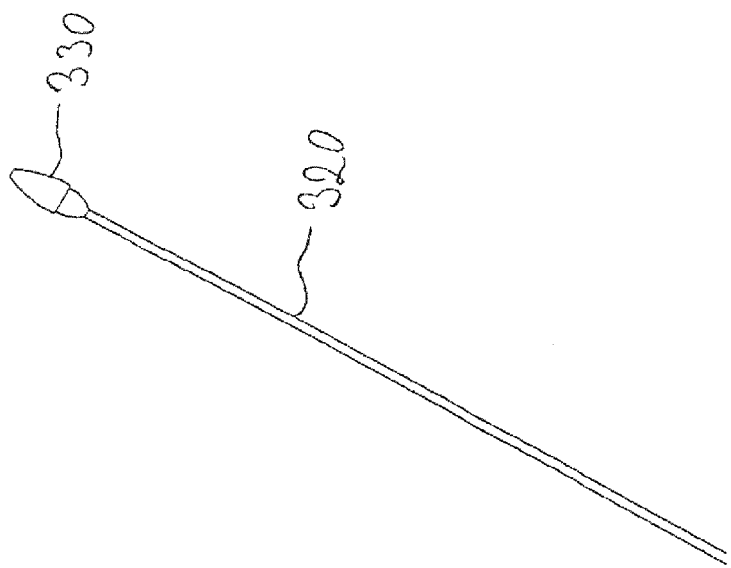

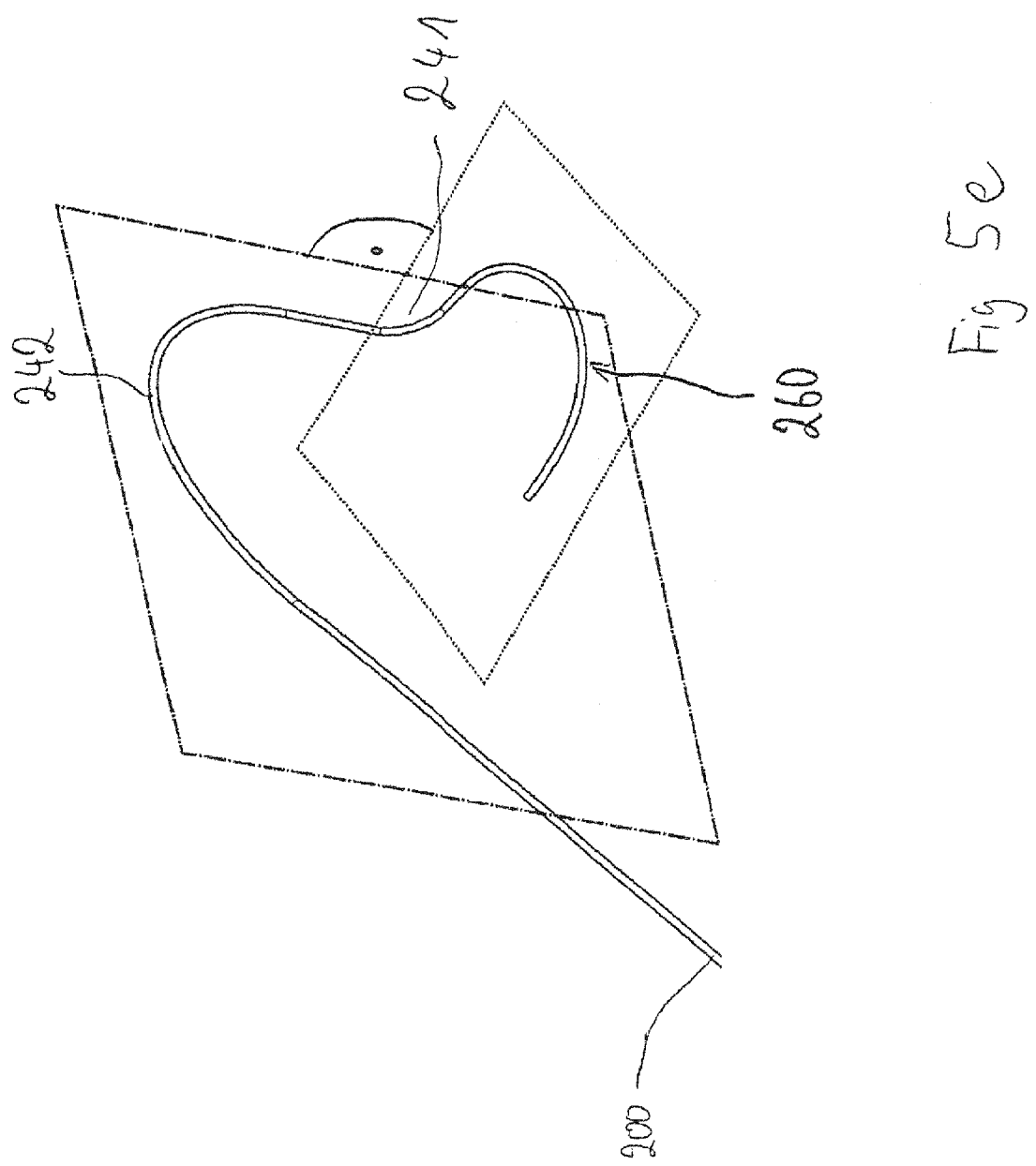

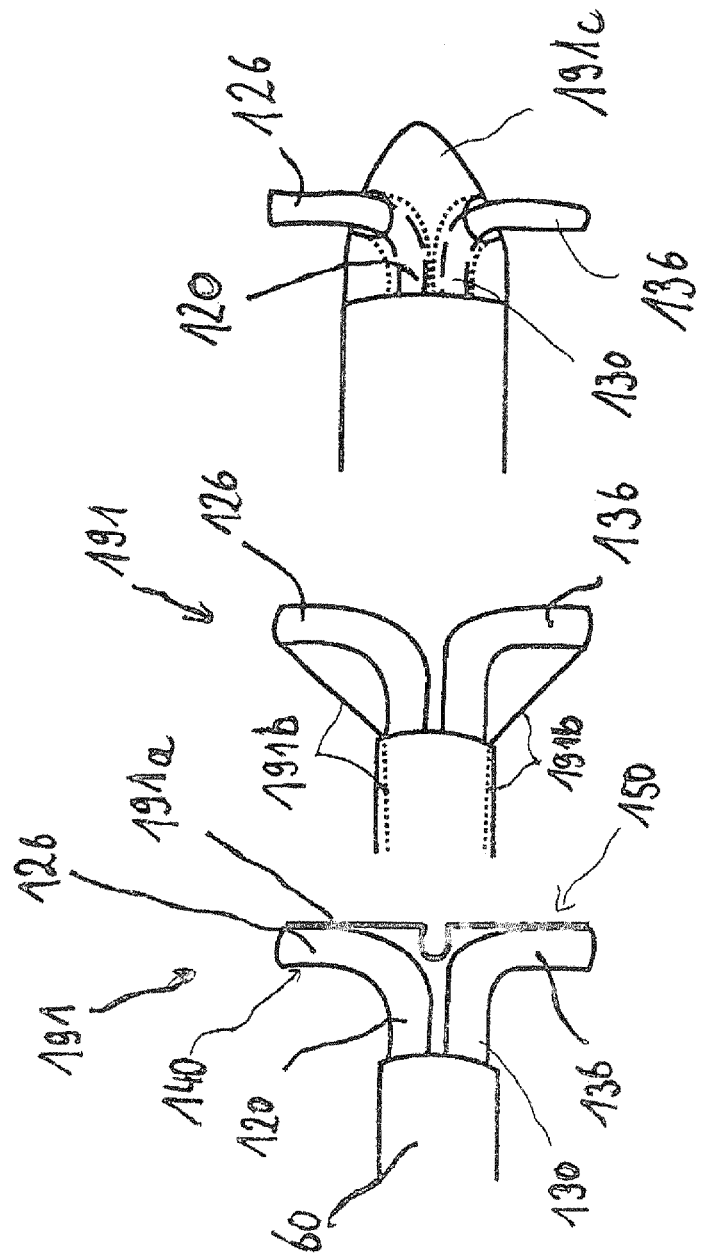

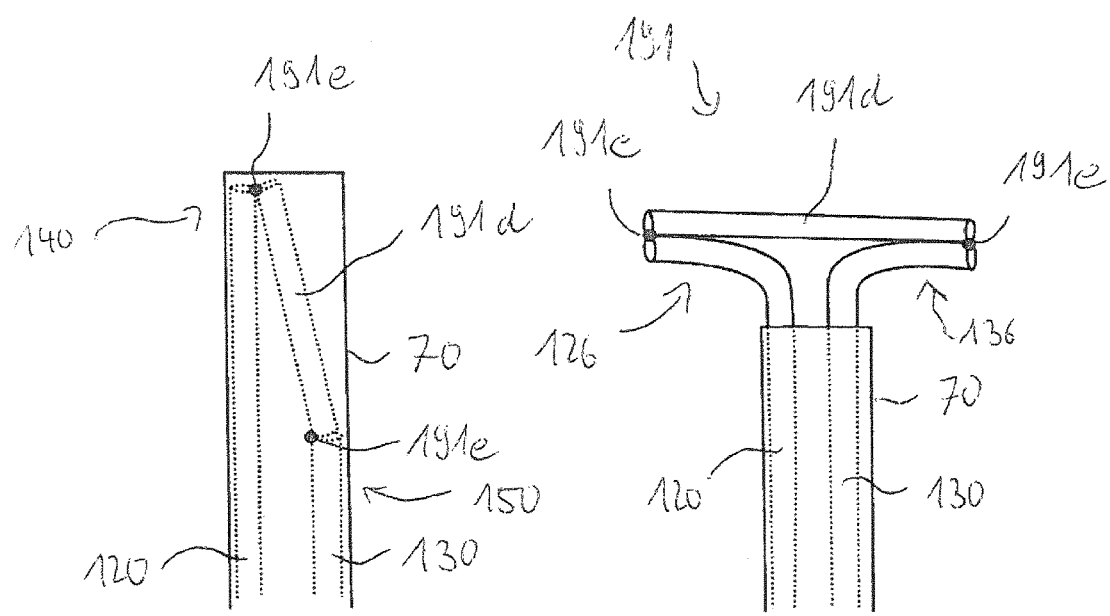

ＵＳ 10,470,884 B2

TREATMENT CATHETER MEMBER WITH ENCIRCLING FUNCTION

REFERENCE TO RELATED APPLICATIONS

This is a Division of application Ser. No. 14/383,614, filed Sep. 8, 2014, which issued as U.S. Pat. No. 9,770,332 on Sep. 26, 2017, which in turn is a national stage application of PCT/EP2013/054442, filed Mar. 5, 2013, which claims the benefit and priority of U.S. Provisional Application No. 61/607,073, filed Mar. 6, 2012, and claims the benefit and priority of German Patent Application No. 10 2012 101 877.4, filed Mar. 6, 2012. The disclosure of the prior applications is hereby incorporated by reference herein in its entirety.

TECHNICAL FIELD

The invention generally relates to a catheter member for interacting with circumferential tissue structure and a method for using a catheter member.

BACKGROUND

Heart valve diseases are affecting approximately 300.000 people worldwide each year. Those diseases translate in abnormal leaflet tissue (excess tissue growth, tissue degradation/rupture, tissue hardening/calcifying), or abnormal tissue position through the cardiac cycle (e.g. annular dilation, ventricular reshaping) leading to a degrading valve function like leakage/blood backflow (valve insufficiency) or a resistance to blood forward flow (valve stenosis). Many of these diseases are treatable via catheter techniques.

Accordingly, a catheter member is desirable.

BRIEF DESCRIPTION

A catheter member for interacting with a circumferential tissue structure comprises an elongate primary catheter which has at least one inner lumen and which extends along a longitudinal axis and has a distal end portion, first and second elongate secondary catheters each extending along a longitudinal axis, each comprising a distal end portion and a proximal end portion and an inner lumen, and each comprising a secondary alignment portion, which is located between the distal and proximal end portions and adjacent to the distal end portion, and each to be disposed in an inner lumen of the primary catheter to be moveable relatively thereto and exposable therefrom (e.g. the distal end portion thereof), a first flexing mechanism to provide the distal end portion of the first and/or second secondary catheter with a tendency to assume a first secondary bent shape, and a second flexing mechanism to provide the secondary alignment portion of the first and/or second secondary catheter with a tendency to assume a second secondary bent, shape. The distal end portion of both of the first and second secondary catheters is configured to be able to be flexed e.g. by the first flexing mechanism to form an arm portion substantially transverse to the direction of the longitudinal axis of the primary catheter so as to assume the first secondary bent shape, when being exposed from the distal end portion of the primary catheter. The secondary alignment portion of the first and second secondary catheter may be configured to be able to be flexed by the second flexing mechanism to assume the second secondary bent shape having a predetermined curvature, optionally with a radius of substantially 30 to 70 mm and optionally describing an angle of 90° to 270°. The arm portions of the first and second secondary catheters, respectively, may extend in generally opposite directions to each other when the secondary alignment portions of the first and second secondary catheters assume the second secondary bent shape in parallel to each other.

Methods are provided for encircling or ensnaring a structure such as a tissue structure or another hard-to-reach structure (described elsewhere herein) with a wire or the like. The methods may include advancing a plurality of secondary catheters through one or more lumina in a primary catheter, optionally advancing respective tertiary catheters through lumina in the secondary catheters, and advancing wires or the like through the tertiary catheters. For example, methods of the invention nay involve advancing secondary catheters through one or more lumina in a primary catheter such that the secondary catheters are exposed at an opening in a side or end of the primary catheter, and one or more secondary catheter is bent at one or more angle relative to the primary catheter as the secondary catheters are exposed. Tertiary catheters may be advanced through and out of openings in the secondary catheters, preferably such that the tertiary catheters bend as they are advanced out of the secondary catheters. The tertiary catheters may preferably bend in a complementary fashion to form all or part of an encircling structure around the tissue structure or other hard-to-reach structure. One or more wires and/or catching mechanisms may then be advanced through the catheters to encircle or ensnare the tissue structure or other hard-to-reach structure generally in the manner described in connection with specific apparatus features herein, but without limitation to those specific apparatus features. The catheters and/or wires or the like may be advanced with or without contact with the tissue structure or other hard-to-reach structure, and may be provided with blunt-nosed leading features such as those described herein so as to avoid trauma to the tissue structure or other hard-to-reach structure in the event contact is made.

BRIEF DESCRIPTION OF THE DRAWINGS

In the drawings, like reference characters generally refer to the same parts throughout the different views. The drawings arc not necessarily to scale, emphasis instead generally being placed upon illustrating the principles of the invention. In the following description, various embodiments are described with reference to the following drawings, in which:

FIG. 1b shows a schematic view of a proximal side of a catheter member according to a variation, FIGS. 4a to 4c show a catheter member according to a variation, FIGS. 5a to 5e show detailed views of components of a catheter member according to an variation, FIGS. 6a to 6c show views of a flexing mechanism according to a variation, FIGS. 7a to 7c show a catheter member according to a variation, FIGS. 14a to 14f show views of flexing mechanisms according to a variation.

DESCRIPTION

The following detailed description refers to the accompanying drawings that show, by way of illustration, details of specific variations in which the invention pray be practiced. These variations are described in sufficient detail to enable those skilled in the art to practice the la invention. Other variations may be utilized and structural, logical, and electrical changes may be made without departing from the scope of the invention. The various variations are not necessarily mutually exclusive, as all variations can be combined with all other variations to form embodiments. In this regard, all features disclosed herein are applicable to all variations and/or embodiments of the invention and features disclosed herein may not be applicable to certain variations or embodiments. Accordingly, any feature described herein has to be understood as to be disclosed alone and/or in combination with any other feature or features. The methods discussed herein are more general, and may be performed with tile specifically described exemplary apparatus or with other apparatus capable of directing the movement of features as described herein.

Figure 1A:
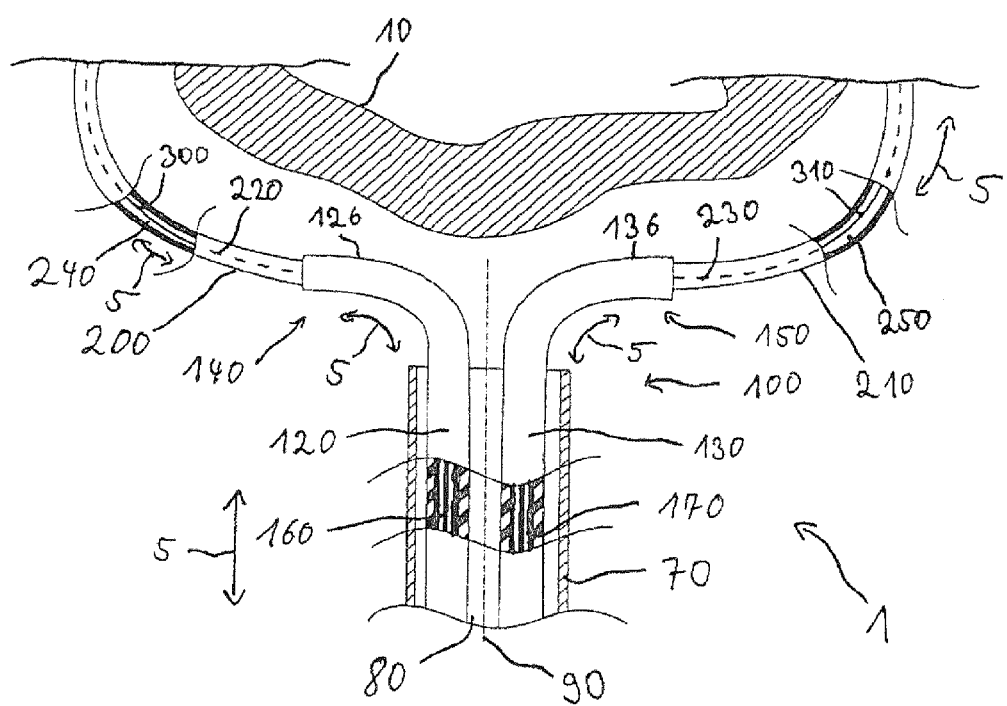
FIG. 1a shows a schematic partially cut cross section view of a distal side of a catheter member according to a variation.
Figure 16:
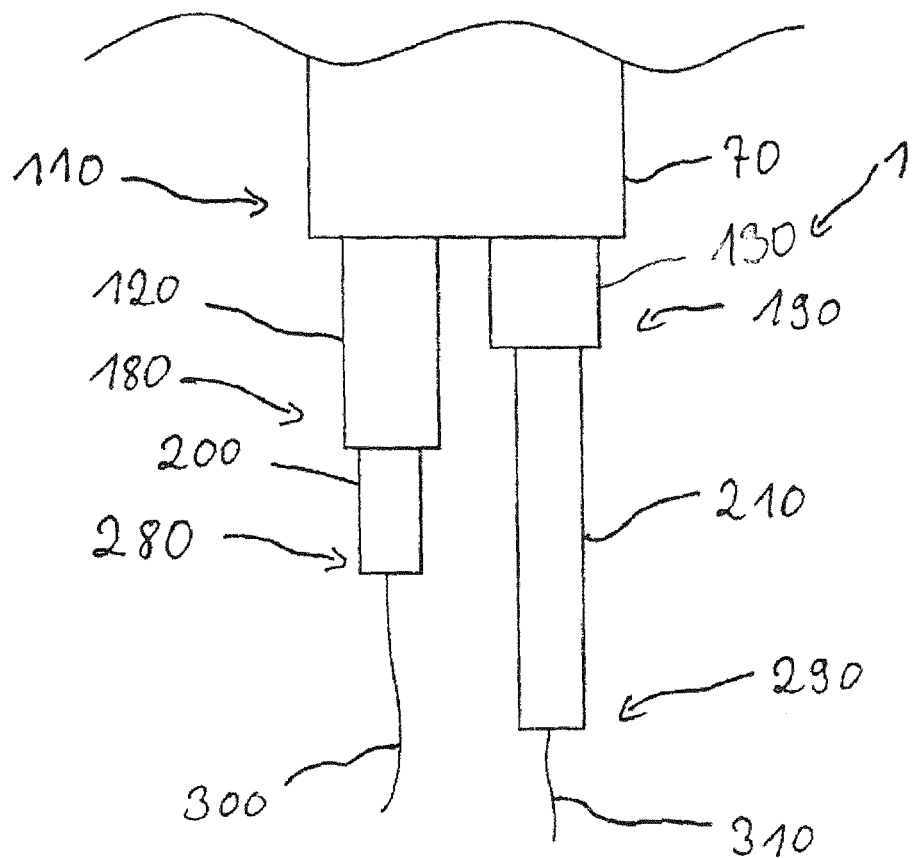

With reference to the figures, e.g. FIG. 1a thereof, a catheter member 1 for interacting with a (e.g. circumferential) tissue structure 10 may be provided that may comprise an elongate) primary catheter 70 which may have an inner lumen 80 and which may extend along a longitudinal axis 90 and may have a distal end portion 100. A catheter member 1 may further comprise first 120 and/or second 130 (e.g. elongate) secondary catheters that each may comprise a distal end portion 140, 150 and an inner mitten 160, 170, and each may be disposed in the inner lumen 80 of the primary catheter 70 and may be moveable relative thereto and may be exposable from the distal end portion 100 thereof. A first flexing mechanism 191 may provide the distal end portion 140, 150 of the first 120 and/or second 130 secondary catheter with a tendency to assume a first secondary bent shape. The distal end portion 140, 150 of one or both of the first and second secondary catheters 120, 130 may be provided so as to be able to be flexed by the first flexing mechanism 191 to form an arm portion 126, 136 that may be substantially transverse to the direction of the longitudinal axis 90 of the primary catheter 70 so as to assume the first secondary bent shape, at least when being exposed, from the distal end portion 100 of the primary catheter 70.

Figures 3A, 3B:
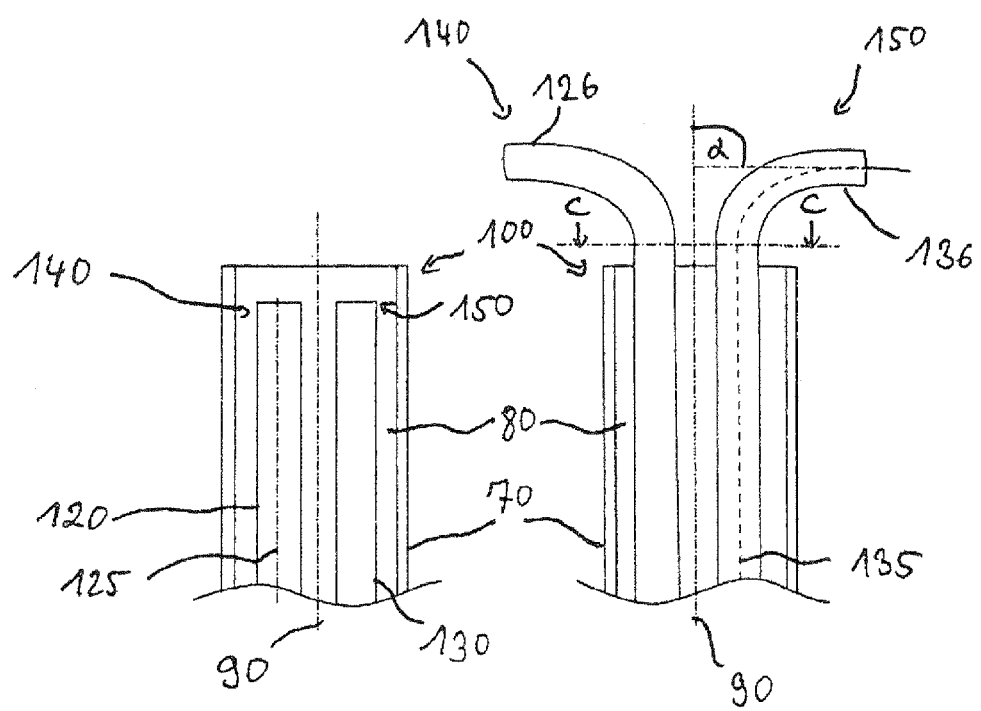
FIGS. 3a and 3b show schematic cross section views of a primary catheter and secondary catheters of a catheter member according to a variation.

An arm portion 126, 136 may, for example, at least 4 mm or at least 5 mm or at least 8 mm or at least 10 mm or at least 12 mm, in a direction radial to the longitudinal axis 90 of primary catheter 70. A free end of the respective aria portion 126, 136 may face away from the longitudinal axis 90 so that the respective arm portion 126, 136 may form a blunt end face extending transversely to the longitudinal axis 90 of the primary catheter 70 that may frontally contact the tissue structure 10 with the catheter member 1 in a non-penetrating manner. First 120 and second 130 secondary (e.g. elongate) catheters may each extend along a longitudinal axis 125, 135 (see e.g. FIG. 3a), may each comprise a distal end portion 140, 150 and a proximal end portion 180, 190 and an inner lumen 160, 170, and may each comprise a secondary alignment portion 127, 137, which may be located between the distal 140, 150 and proximal end portions 180, 190 and adjacent to the distal end portion 140, 150. The first and second secondary catheters may each be disposed in an inner lumen 80 of the primary catheter 70 and may be moveable relative thereto and exposable from the distal end portion 100 thereof.

A second flexing mechanism 192 may provide the secondary alignment portion of the first 120 and/or second 130 secondary catheter with a tendency to assume a second secondary bent shape. A distal end portion 140, 150 of both of the first and second secondary catheters 120, 130 may be provided so as to be able to be flexed by the first flexing mechanism 191 to form an arm portion substantially transverse to the direction of the longitudinal axis 90 of the primary catheter 70 so as to assume the first secondary bent shape, when being exposed from the distal end portion 100 of the primary catheter 70. A secondary alignment portion 127, 137 of the first 120 and second 130 secondary catheters may be provided so as to be able to be flexed by the second flexing mechanism 192 to assume the second secondary bent shape that may have a predetermined curvature, optionally with a radius of substantially 30 to 70 mm and optionally describing an angle of 90 to 270°. The arm portions 126, 136 of the first 120 and second 130 secondary catheters, respectively, may extend in generally opposite directions to each other when the secondary alignment portions 127, 137 of the first 120 and second 130 secondary catheters assume the second secondary bent shape, e.g. in parallel to each other.

Figure 2:
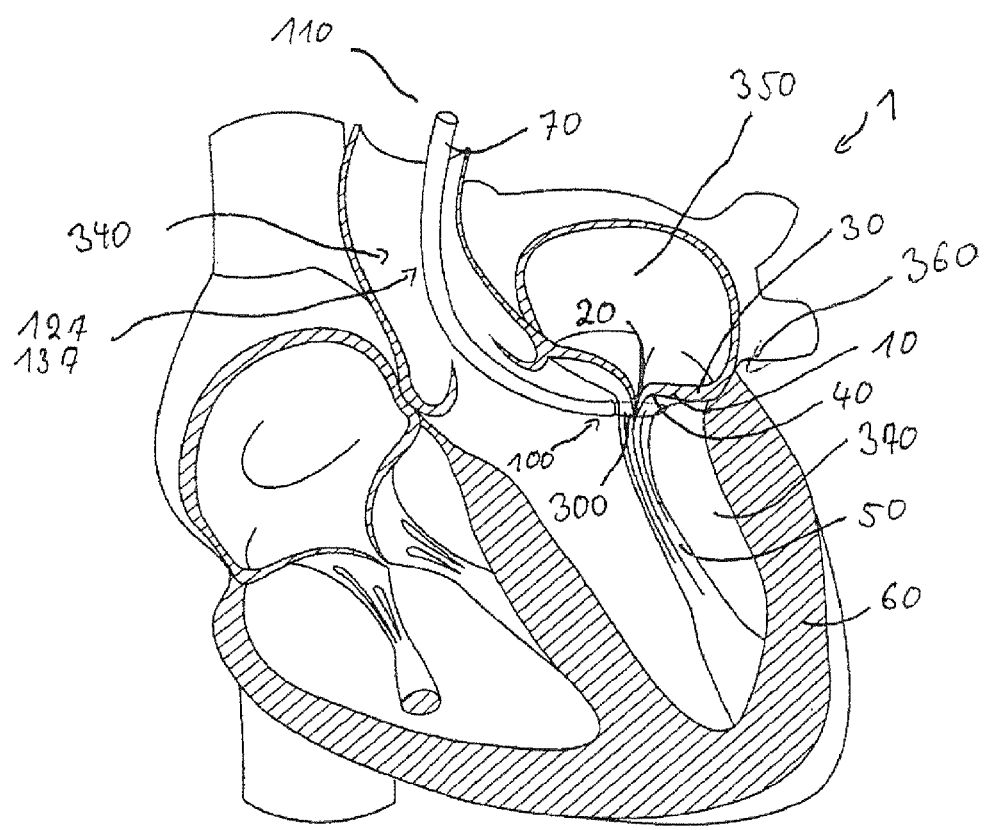
FIG. 2 shows a schematic cross section view of heart and a catheter member according to a variation.

With further reference to the figures, a catheter member 1 for interacting with (e.g. surrounding, e.g. treating) an anatomic feature (in the following for better understanding also referred to as tissue structure, accordingly said anatomic feature may be a tissue structure, e.g. a circumferential tissue structure) 10 may be provided. The tissue structure 10 may for example be a part of a heart, e.g. part of a heart valve such as a ventricular valve, mitral valve, pulmonal valve and/or triscupidal valve. With reference to FIG. 2, the tissue structure 10 may e.g. comprise a part of or may be a heart valve having a connection channel 20 comprising a connection channel wall structure forming said connection channel 20 or "through opening". The heart valve may comprise a circumferential valve annulus 30, valve leaflets 40 opening and closing the connection channel at a position close to the valve annulus 30 to provide a valve-functionality, a generally circumferential chord structure (chordae tendinae) 50 connecting the valve leaflets 40 and generally papillary muscle(s) 60, and said papillary muscles 60. The circumferential tissue structure 10 may be said connection channel, wall structure.

The catheter member 1 may comprise a primary catheter member 70 (see e.g. FIG. 5a). The primary catheter member or primary catheter 70 may e.g. be flexible and have a generally tubular shape. The primary catheter member 70 may comprise one or more inner lumen 80 and to may extend along a longitudinal axis 90. The primary catheter may comprise a distal end portion 100 and may comprise a proximal end portion 110 (see e.g. FIG. 1b). The distal and/or proximal end portions 100, 110 may comprise end openings provided to connect the inner lumen(s) 80 of the primary catheter 70 to the outer side; surrounding of the primary catheter 70 (each of the catheters described herein, e.g. secondary or tertiary catheter, may comprise end openings).

While the primary catheter 70 is shown in FIG. 1 to comprise one inner lumen 80, the primary catheter 70 may comprise multiple inner lumina 80 that are separate from each other. The multiple inner lumina 80 may all have the same inner diameter or may have different inner diameters. The inner side of primary catheter 70 (i.e. the "outer side" of inner lumen 80) may be a smooth surface and/or coated so as to have a low coefficient of friction so as to facilitate forwarding and/or retraction of secondary catheters (described in more detail below) or the like. In this regard, the primary catheter 70 may comprise a braid-type flexible hose or a corrugated-type flexible hose (e.g. made from stainless steel) and may comprise a smooth inner liner, e.g. made from Pebax or PTFE or the like (not shown).

The primary catheter 70 may be flexible and/or rigid, and the distal end portion 100 may be flexible and/or rigid and/the the proximal end portion 110 may be flexible and/or rigid. While the primary catheter 70 may be generally flexible, the distal 100 and/or proximal 110 end portions may be rigid to facilitate approach to the tissue structure 10 and/or handling by a interventional cardiologist, respectively.

The primary catheter member 70 may be made from a shape memory material, e.g. a shape memory alloy (such as, e.g., nitinol or Fe—Mn—Si or any metal or alloy with shape memory properties) car a shape memory polymer (such as, e.g., Norsorex or PET cross-linked with glycerol/dimethyl-5-sulfoisopthalate or maleic anhydride or any other shape memory polymer). While the primary catheter 70 may be made of a distinctive shape memory material that is e.g. providing material elasticity as it is known in the art, it may also (additionally or as an alternative) comprise structural shape memory properties, i.e. it may be made from a material without distinctive shape memory characteristics (e.g. spring steel) but have shape memory characteristics due to its geometric design and/or elasticity features. However, the primary catheter 70 may be a conventional catheter not comprising shape memory material or structural shape memory properties. The primary catheter 70 may be flexible; e.g. it may be a flexible tube or hose or the like.

Figure 5B:
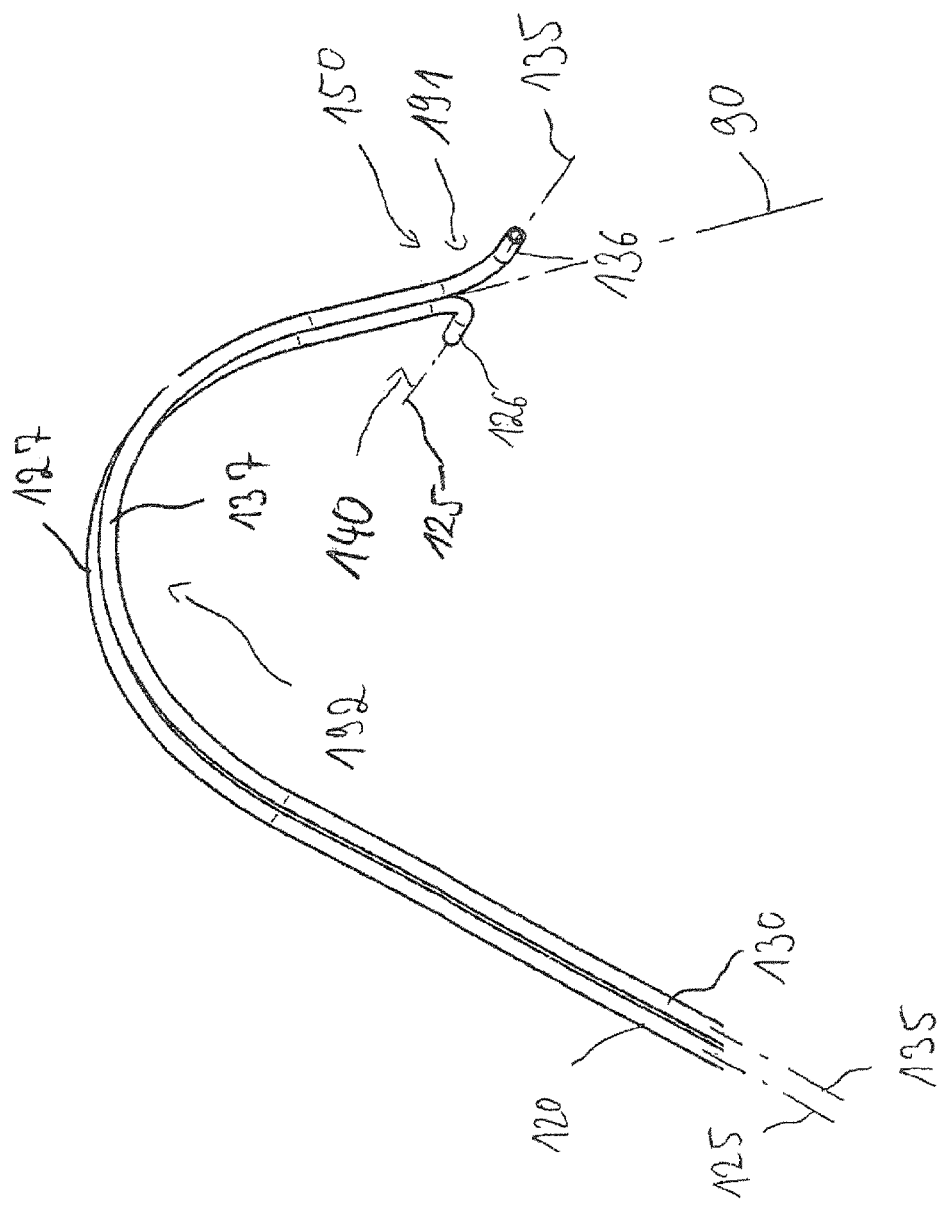

The catheter member 1 may also comprise a first 120 and/or a second 130 (or secondary catheter(s) (see e.g. FIG. 5*b*). The first 120 and/or second 130 secondary catheters may comprise a first secondary catheter distal end portion 140 and a second secondary catheter distal end portion 150, respectively. The distal end portion 140, 150 of one or both of the first and second secondary catheter 120, 130 may be provided to be flexible (i.e. configured to be able to be flexed, e.g. flexible) by a first flexing mechanism 191 (described below). Accordingly, the distal end portion 140 of the first secondary catheter 120 and/or the distal end portion 150 of the second secondary catheter 130 (or a part of both or any of the distal end portions 140, 150) may be elastic or may be plastically deformable.

The first 120 and/or second 130 secondary catheter may comprise a first secondary catheter inner lumen 160 and a second secondary catheter inner lumen 170, respectively. The first 120 and/or second 130 secondary catheter may each comprise one or multiple, separate inner lumina 160, 170. The first secondary catheter 120 may extend along a longitudinal axis 125 (that may be an axis extending longitudinally through a radial center/middle point of the first secondary catheter 120). Similarly, the second secondary catheter 130 may extend along a longitudinal axis 135 (that may be an axis extending longitudinally through each radial center/middle point of the second secondary catheter 130). The first 120 and/or second 130 secondary catheter may also each comprise a proximal end portion 180, 190 (see e.g. FIG. 1*b*) that may be located substantially oppositely along a longitudinal axis 125, 135 of a respective secondary catheter 120, 130 to the respective distal end portion 140, 150.

The outer diameter of the first 120 and second 130 secondary catheter, respectively, may be smaller than a diameter of an inner lumen 80 of primary catheter 70, so that the secondary catheters 120, 130 may be provided in the inner lumen 80 of primary catheter 70 and may be moveable, e.g. forwardable and retractable, with respect to the (e.g. distal end portion 100 of the) primary catheter 70. The secondary catheters 120, 130 may be longitudinally longer than the primary catheter 70 so that their respective proximal end portions 180, 190 may be handled by a surgeon in order to operate (e.g. forward and/or retract) their distal end portions 140, 150 relative to the distal end portion 100 of the primary catheter 70.

The catheter member 1 may also comprise a first flexing mechanism 191 (described below) to give the distal end portion 140, 150 of the first 120 and/or second 130 secondary catheter a tendency to assume a first secondary bent shape. The first flexing mechanism 191 also may provide the first secondary bent shape.

The first secondary bent shape may be a shape in which the distal end portions 140, 150 of the first and/or second secondary catheter 120, 130 each form an arm portion 126, 136. An arm portion 126, 136 and/or both arm portions 126, 136 may comprise a lateral outer surface, i.e. a surface that may span a circumference (e.g. a surface that is extending circumferentially around longitudinal axis 125, 135 of first 120 and second 130 secondary catheters, respectively) of a respective arm portion 126, 136. For example, when using the catheter member 1, said lateral outer surface or outer surfaces may be contacting a structure which is to be surrounded using catheter member 1. The arm portion 126 of the distal end portion 140 of the first secondary catheter 120 and/or the arm portion 136 of the distal end portion 150 of the second secondary catheter 130 may extend substantially transverse to the longitudinal axis 90 of the primary catheter 70, at least when the respective distal end portion 140, 150 has assumed the first secondary bent shape (schematically shown e.g. in FIG. 3*b*). The arm portion 126, 136 (or both arm portions 126, 136 at the same time) of the distal end portion 140, 150 of the first 120 and/or second 130 secondary catheter, respectively, may face away from the longitudinal axis 90 of the primary catheter 70 so that arm portion 126, 136 of the distal end portion 140, 150 of the first 120 and/or second 130 secondary catheter (or both arm portions 126, 136) may form a blunt end face that extends transversely to the longitudinal axis 90 of the primary catheter 70 and that may frontally (e.g. with respect to catheter member 1, e.g. in a direction corresponding to longitudinal axis 90 of primary catheter 70) contact the tissue structure 10 in a non penetrating manner with a lateral outer surface thereof, as the arm portion 126, 136 (see e.g. FIG. 11) (or both arm portions 126, 136 at the same time (see e.g. FIG. 9 or FIG. 13*b*)) may form a blunt contact area that cannot penetrate tissue structure 10 or cause trauma damage. Both aim portions 126, 136 may extend substantially transverse to the longitudinal axis 90 of the primary catheter 70. However there may also be only one (any one) arm portion 126. 136 extending transverse to longitudinal axis 90, while at the same time the other arm portion 126, 136 may extend substantially parallel to said longitudinal axis 90 of the primary catheter 70.

One or all of the arm portions 126, 136 may be rectilinear, i.e. the respective distal end portion 140, 150 may comprise a rectilinear arm portion 126, 136 and a curved part adjacent to the rectilinear arm portion 126, 136. The curved part may serve to give the rectilinear arm portion 126, 136 a defined orientation relative to the respective first or second secondary catheter 120, 130.

When the catheter member 1 is in an operational position and located adjacent to a tissue structure 10, one or all arm portions 126, 136 may be oriented in such a way that the longitudinal axis 125, 135 of the respective secondary catheters 120, 130 extends substantially in a straight line and transversely to the longitudinal axis 90 of the primary catheter 70. The arm portion(s) 126, 136 may also extend substantially parallel to a tangent of a circumferential tissue structure 10. The tangent may be the tangent that intersects a circumference of tissue structure 10 in the same point on the circumference of tissue structure 10 that is the point that intersects with the extension of the longitudinal axis 90 of primary catheter 70, when in an operational position. The arm portion(s) 126, 136 may have (e.g. each) a (e.g. substantially rectilinear) extension length of more than 4 mm, more than 5 mm or more than 7 mm, e.g. 4 to 7 mm or 5 to 7 mm or 4 to 20 mm. The arm portion(s) 126, 136 may serve to reduce trauma and stress that may be induced on the circumferential tissue structure 10 by movement of the catheter member 1 by providing a larger contact area in case of physical contact. Thereby, the arm portions 126, 136 (or one of the arm portions) may reduce the mechanical stress induced on circumferential tissue structure 10 (stress equals force divided by area, and the catheter member 1 provides a large contact area through the arm portions and thereby reduces stress) in case of contact between catheter member 1 and tissue structure 10, thereby preventing trauma and potentially lethal tissue damage by enabling catheter member 1 to contact tissue structure 10 in a non-penetrating manner. One or both arm portion(s) 126, 136 may, due to their design/shape/orientation, also act as an elastic buffer and dissipate some energy by elastic deformation in case of contact between catheter member 1 and the tissue structure 10. Further, the arm portion(s) 126, 136 may allow the user to precisely guide one or more tertiary catheter 200, 210 (described in more detail below) around the tissue structure 10 by providing enhanced stability and guiding-capability (if one or more tertiary catheter 200, 210 is provided).

Accordingly, the rectilinear arm portion 126 of the distal end portion 140 of the first secondary catheter 120 may define an angle α with the longitudinal axis 90 of the primary catheter 70 (see e.g. FIG. 3*b* or 4*b*), at least when the distal end portion 140 has assumed the first secondary bent shape. Likewise, the rectilinear arm portion 136 of the distal end portion 150 of the second secondary catheter 130 may define an angle α with the longitudinal axis 90 of the primary catheter 70, at least when the distal end portion 150 has assumed the first secondary bent shape. The arm portion 126 of distal end portion 140 of the first secondary catheter 120 may define a different angle α than the arm portion 136 of distal end portion 150 of the second secondary catheter 130, or both arm portions 126, 136 may define the same angle α, at least when one or both of the distal end portions 140, 150 have assumed the first secondary bent shape. The angle α may be substantially 90° or ≥80° or ≥60° or ≥50° or ≥45' or any other angle. The angle α may optionally be measured from a distal side of longitudinal axis 90 to a respective rectilinear arm portion 126, 136 (as e.g. shown in FIG. 3*b*) and may optionally have a maximum value of 90° and a minimum value as described above.

As mentioned above, the catheter member 1 may comprise a first flexing mechanism 191. The first flexing mechanism 191 may serve to provide the distal end portion 140 of the first secondary catheter 120 and/or the distal end portion 150 of the second secondary catheter 130 with a tendency to assume a first secondary bent shape, at least when the respective distal end portion 140, 150 is forwarded (e.g. exposed) from the inner lumen 80 of the primary catheter 70. The first flexing mechanism 191 may e.g. comprise a shape memory structure provided on the distal end portion 140, 150 of first 120 and/or second 130 secondary catheter. The first flexing mechanism 191 may be driven by elastic energy that is stored in the first flexing mechanism 191 due to the deformation of the shape memory structure from a predetermined shape caused by a constraint. The constraint may be e.g. the primary catheter 70 that prevents the shape memory structure of flexing mechanism 191 from assuming its predetermined shape. When the constraint is removed (e.g. by forwarding secondary catheter 120, 130 from distal end portion 100 of primary catheter 70) the shape memory structure of first flexing mechanism 191 may give the distal end portion 140, 150 of first 120 and/or second 130 secondary catheter its predetermined shape.

FIG. 6*a* shows a variation of flexing mechanism 191 that comprises a biasing element 191*a* (e.g. a spring). Biasing element 191*a* may give the distal end portions 140, 150 of first 120 and second 130 secondary catheter a tendency to assume the first secondary bent shape. For this, biasing element 191*a* may be connected to the distal end portion 140 and to the distal end portion 150 of first 120 and second 130 secondary catheters, respectively, and may bias said distal end portions 140, 150 to extend generally oppositely (e.g. in opposite directions) to each other, at least when the distal end portions 140, 150 are forwarded (e.g. exposed) from an inner lumen 80 of primary catheter 70.

FIG. 6*b* shows another variation of a flexing mechanism 191. As shown in FIG. 6*b*, first flexing mechanism 191 may comprise an elastic distal end portion 140, 150 on first 120 and/or second 130 secondary catheter which, without any external constraint, may have a tendency to extend rectilinearly (e.g. along longitudinal axes 125, 135 of first 120 and second 130 secondary catheter, respectively). According to FIG. 6*b*, flexing mechanism 191 may further comprise one or more longitudinal elements 191*b* (e.g. a flexible wire or thread) that are connected with the distal end portion 140, 150 of first 120 and/or second 130 secondary catheter and are provided in parallel to the respective secondary catheter 120, 130. The longitudinal elements 191*b* may be provided so that they extend through the inner lumen 80 of primary catheter 70 (indicated by dots in FIG. 6*b*) in order to be operable from a proximal end of catheter member 1 (e.g. primary catheter 70) by an operator. Operation of the longitudinal elements 191*b* may comprise transmitting a force to the distal end portion 140, 150 of the first 120 and/or second 130 secondary catheter by moving the longitudinal elements 191*b* parallel to a longitudinal axis, e.g. longitudinal axis 90 of primary catheter 70 (this may e.g. comprise pulling or pushing longitudinal elements 191*b*). Correspondingly, the distal end portion 140, 150 of the first 120 and/or second 130 secondary catheter may be biased by the longitudinal element(s) 191*b* from their state of generally rectilinear extension to assume the first secondary bent shape.

Figure 11:
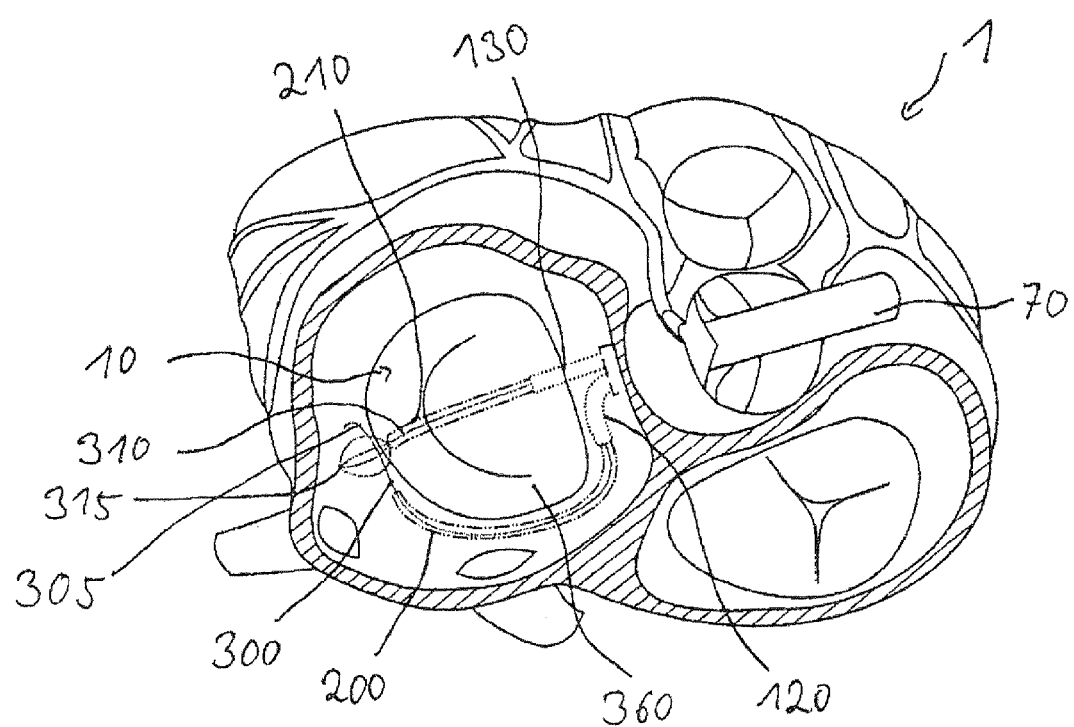

FIG. 6*c* shows another variation of the first flexing mechanism 191. According to FIG. 6*c*, flexing mechanism 191 may comprise a flexing structure 191*c*. Flexing structure 191*c* may be provided on a distal end portion 100 of primary catheter 70 and may comprise a separate channel for each of the secondary catheters 120, 130 configured so that a respective secondary catheter 120, 130 may be forwarded through (e.g. exposed to the exterior of catheter member 1 at a distal end thereof) the flexing structure 191c. Each channel may be provided so that it guides a secondary catheter 120, 130 to assume the first secondary bent shape when the distal end portion 140, 150 (which may be flexible) of first 120 and/or second 130 secondary catheter is forwarded from the distal end portion 100 of primary catheter 70 and through said channel of flexing structure 191c. Flexing structure 191c may comprise a distal conical end portion serving as an atraumatic nose cone to facilitate insertion of the catheter member 1. In this respect, when catheter member 1 comprises a flexing structure 191c and is in an operational state adjacent to a circumferential tissue structure 10, one or more arm portions 126, 136 may extend generally transverse to the longitudinal axis 90 of primary catheter 70 longitudinally spaced from the distal conical end portion of flexing structure 191c so that one or both arm portions 126, 136 may be closer to the tissue structure 10 than the distal conical end portion. Accordingly, when using the catheter member 1 having flexing structure 191c, the arm portions 126, 136 (or one of them, e.g. if e.g. a configuration as shown in FIG. 11 is provided) may contact a tissue structure 10 while at the same time the conical end portion optionally may not contact the tissue structure. Flexing structure 191c may also comprise a separate channel through which front body tube 320 (described later) may extend (not shown). Accordingly, flexing structure 191c may serve to facilitate atraumatic insertion of catheter member 1, while arm portion(s) 126, 136 may be allowed to contact a tissue structure 10 when one or both respective distal end portions 140, 150 of a secondary catheter 120, 130 have assumed their first secondary bent shape.

It must be noted that any flexing mechanism (and in general, any feature) that is described herein can and may be combined with any variation or embodiment of any catheter described herein (e.g. catheter member 1 and/or secondary catheters 120, 130 and/or tertiary catheters 200, 210), unless stated otherwise.

As shown for example in FIG. 2, the first and/or the second secondary catheter 120, 130 may optionally also each comprise a secondary alignment portion 127, 137. The secondary alignment portion 127, 137 of the first and/or second secondary catheter 120, 130 may be located between the distal end portion 140, 150 and the proximal end portion 180, 190 of the first 120 and second 130 secondary catheter, respectively. The secondary alignment portion 127, 137 of the first and/or second secondary catheter 120, 130 may be located adjacent to the distal end portion 140, 150 of the respective first or second secondary catheter 120, 130. The secondary alignment portions 127, 137 may be provided so as to be able to be flexed or bent or deformed by the second flexing mechanism 192 (described in more detail below) to assume a second secondary bent shape.

Further, as mentioned above, the catheter member 1 may optionally comprise a second flexing mechanism 192. The second flexing mechanism 192 may be provided in order to give the secondary alignment portion of the first 120 and/or the second 130 secondary catheter a tendency to assume a second secondary bent shape. The second flexing mechanism 192 may be a shape memory structure, i.e. a structure that has a tendency to elastically or plastically return to a predetermined shape when deformed from this predetermined shape. For this, the second flexing mechanism 192 may comprise a shape memory material like e.g. Nitinol or spring steel or steel and/or may comprise a structure, whose shape memory properties are caused mainly by geometric features of the shape memory structure, e.g. a spiral clement or a spring element. The second flexing mechanism 192 may also comprise active means to give the secondary alignment portions 127, 137 (or any one of them) a tendency to assume the second secondary bent shape according to a control signal. Accordingly, the second flexing mechanism 192 may comprise active elements such as hydraulic actuators or shape memory material in combination with controllable heating/cooling elements (e.g. Peltier elements) to give the secondary alignment portions 127, 137 (or one of them) the tendency to assume the second secondary bent shape. Second flexing mechanism 192 may be provided by material elasticity. Any or all features disclosed with reference to the second flexing mechanism 192 may also be applicable to the first flexing mechanism 191 and versa.

The second secondary bent shape may be a predetermined shape (predetermined e.g. by characteristics/design of the secondary alignment portion(s) 127, 137 and/or the second flexing mechanism 192). The second secondary bent shape may be chosen or predetermined to correspond to a geometric constraint is not part of catheter member 1, e.g. the second secondary bent shape may correspond to an anatomic feature. In this respect, the second secondary bent shape may be chosen so as to resemble (e.g. correspond to) the curvature of an anatomic feature, e.g. an aortic arch 340 of a human heart, of an ovine or porcine heart or generally of a mammal heart. Accordingly, the secondary alignment portion 127, 137 of the first 120 and/or second 130 secondary catheter may mate (and/or fit together) with an anatomic feature (e.g. aortic arch 340) when the secondary alignment portion 127, 137 has assumed the respective secondary bent shape.

The secondary alignment portion 127, 137 may serve to align a position and/or orientation of the respective first and/or second secondary catheter 120, 130 by having a tendency to assume the second secondary bent shape, that corresponds e.g. to an aortic arch 340, and may be induced by the second flexing mechanism 192. Thereby, when the first or second secondary catheters are located e.g. in an anatomic feature, e.g. in an aortic arch 340, they can assume their chosen or predetermined shape caused by the flexing mechanism 192, thereby resembling the shape of the aortic arch, or in other words, mating with the natural shape of the anatomic feature. This will align the secondary alignment portion 127, 137 (and accordingly the first and/or second secondary catheter 120, 130) with the anatomic feature, as the secondary alignment portion may be in a stable (e.g. energetically favorable) position, when it is able to assume the secondary bent shape (whereby the tendency to assume that shape is induced by the second flexing mechanism 192). The second alignment portion 127, 137 and/or the second flexing mechanism 192 may e.g. have a minimum of elastic energy when the second alignment portions 127, 137 have assumed their respective second bent shape. Accordingly, the "mating" of a secondary alignment portion 127, 137 with an anatomic feature may give the respective first 120 and/or second 130 secondary catheter a defined and predetermined position and/or a defined and predetermined rotational position and e.g. may rotate a respective secondary catheter 120, 130.

Accordingly, the design of the secondary alignment portion 127, 137 of the first 120 and/or second 130 secondary catheter, respectively, and/or of the second flexing mechanism 192 may be chosen so as to give the distal end portion 140, 150 of the first 120 and/or second 130 secondary catheter a predetermined orientation and/or rotational orientation and may therefore also give the first 120 and/or second 130 secondary catheter a predetermined orientation and/or position.

In this respect, the distal end portion 140, 150 of the first 120 and/or second 130 secondary catheter may have a defined and predetermined orientation and position, e.g. with respect to circumferential tissue structure 10. When the respective distal end portion 140, 150 assumes the first secondary bent shape, the orientation and rotation of the arm portion 126, 136 may therefore also be defined and/or predetermined as first and/or second secondary catheter 120, 130 may have a defined position and/or orientation, caused e.g. by the secondary alignment portion. As a consequence, the distal end portion 140, 150 (and/or arm portions 126, 136) may be positioned and oriented relative to an anatomic feature (e.g. tissue structure 10) without any additional means. Further, in the state of alignment or mating with an anatomic feature, there may also be some resistance provided against longitudinal movement of the aligned/mated catheter, e.g. against unintended longitudinal movement by a person handling catheter member 1 (the resistance may e.g. depend amongst others on the elastic properties of the respective catheter).

Figure 3C:
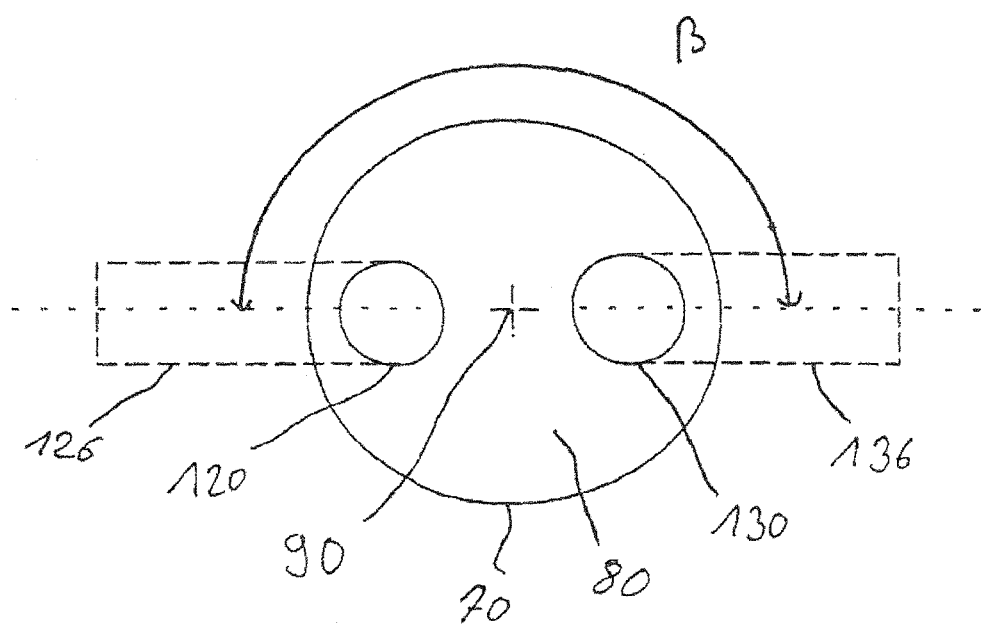
FIG. 3c shows a radial cross section view along C-C of FIG. 3b of a primary catheter and secondary catheters of a catheter member according to a variation.

The arm portions 126, 136 of the first 120 and second 130 secondary catheter, respectively, (e.g. the respective longitudinal axes 125, 135) may define an angle β between each other (see e.g. FIG. 3c, that shows a section along C-C in FIG. 3b), at least when they have assumed their first bent shape. The angle β may be caused, and may be predetermined by design of the secondary alignment portions 127, 137 and/or the second flexing mechanism 192 as this may lead to a defined position and orientation of the first 120 and/or second 130 secondary catheter (or the respective distal end portion 140, 150). The angle β may be approximately 180° or ≥170° or ≥160° or ≥120° or ≥90° or ≥45° or any other angle depending on the desired positioning of the first 120 and second 130 secondary catheters in use.

Accordingly, the orientation and position of an arm portion 126, 136 relative to an anatomic feature (e.g. tissue structure 10) and/or relative to the other respective arm portion 126, 136 may be defined by the first and/or second secondary alignment portions 127, 137, at least when they are in their respective second bent shape.

Figure 4B:
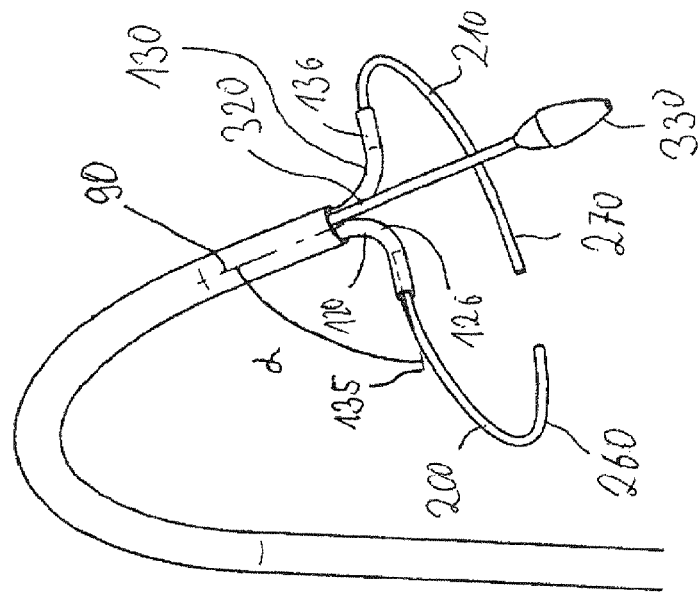
Figure 4A:
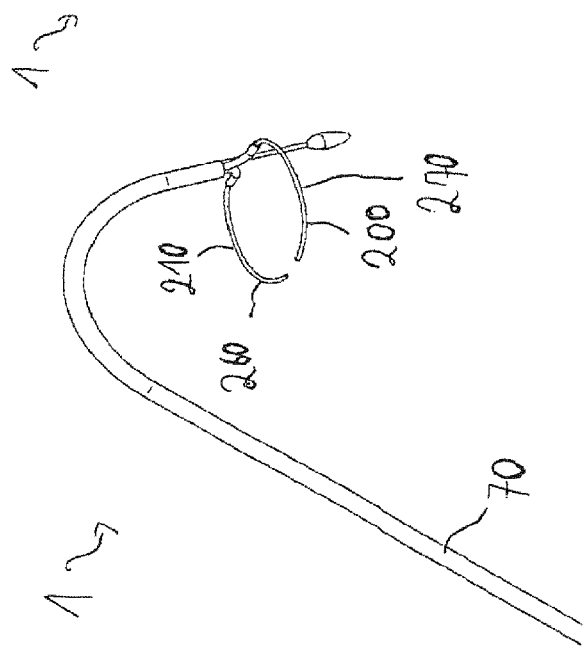

Further, the catheter member 1 may optionally comprise a first 200 and/or a second 210 tertiary catheter (see e.g. FIG. 4a, 4b, 4c). The catheter member 1 may also comprise only one or more than two tertiary catheters, e.g. three to five tertiary catheters. The first 200 and second 210 tertiary catheter may each extend along a longitudinal axis 220 and 230, respectively. The first 200 and second 210 tertiary catheter may also comprise each one or more inner lumina 240 and 250, respectively. Further, the first tertiary catheter 200 may comprise a distal end portion 260 and a proximal end portion 280 and the second tertiary catheter 210 may comprise a distal end portion 270 and a proximal end portion 290 (see e.g. FIG. 1b). The proximal 280, 290 and distal 260, 270 end portions of a respective tertiary catheter may be located on substantially opposite ends along longitudinal axis 220, 230 thereof.

A tertiary catheter 200, 210 (i.e. one tertiary catheter and/or both tertiary catheters) may be guided by a respective secondary catheter 120, 130. In order to be guided, one tertiary catheter 200, 210 may be provided on one secondary catheter 120, 130 so that the secondary catheter 120, 130 is received in the inner lumen 240, 250 of the respective tertiary catheter 200, 210. A tertiary catheter 200, 210 may be provided in parallel to a secondary catheter 120, 130 and a parallel-guiding-device may be provided in order to guide a tertiary catheter 200, 210 parallel (e.g. with respect to longitudinal axis 125, 135) along a secondary catheter 120, 130. A parallel-guiding-device may for example be a flexible hose that fits tightly around a secondary and a tertiary catheter in order to enable parallel guiding of a tertiary catheter along the longitudinal axis 125, 135 of a secondary catheter 120, 130.

The first tertiary catheter 200 may be provided in an inner lumen 160 of the first secondary catheter 120 and the second tertiary catheter 210 may be provided in an inner lumen 170 of the second secondary catheter 130 so as to be moveable relative to the first 120 and second 130 secondary catheter, respectively. The first 200 and/or second 210 tertiary catheters may be configured so that their respective distal end portion 260, 270 may be forwarded from and/or retracted in an inner lumen 160, 170 of the first 120 and second 130 secondary catheter, respectively, so that their respective distal end portion 260, 270 may be exposed from the distal end portion 140, 150 of the corresponding r second secondary catheter 120, 130. Accordingly, an outer diameter of the first 200 and/or second 210 tertiary catheters ay be smaller than the outer diameter of the respective inner lumen 160, 170 of the respective secondary catheter 120, 130. The outer diameter of the first 200 and/or second 210 tertiary catheters may also be slightly larger than the inner diameter of the respective inner lumen 160, 170 of the respective secondary catheter 120, 130 in order to provide a slight press fit in order to maintain relative moveability of the catheters but also to provide an opposing force to any relative movement to facilitate precise relative movement.

Each tertiary catheter 200, 210 may be guided in the same manner by a respective secondary catheter 120, 130 or may be guided in a different manner. For example, the first tertiary catheter 200 may be provided in the inner lumen 160 of first secondary catheter 120 while at the same time second secondary catheter 130 may be received in inner lumen 250 of second tertiary catheter 210 so that the tertiary catheters 200, 210 are guided by the secondary catheters 120, 130.

Figure 5C:
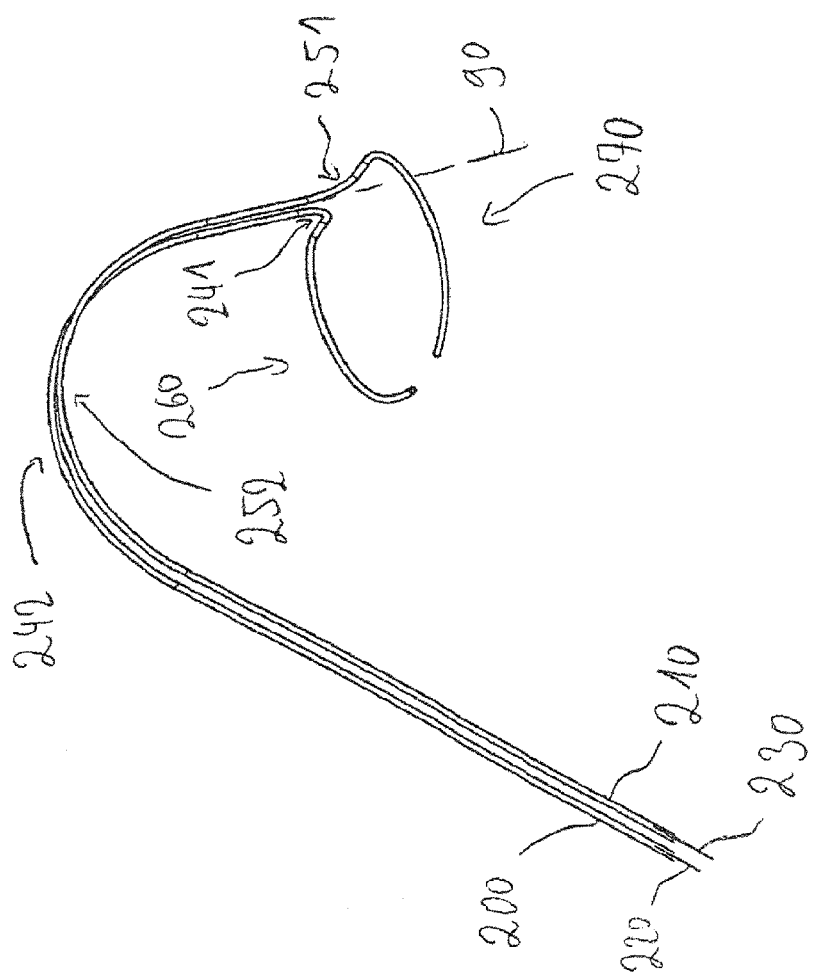

As shown for example in FIG. 5c, first 200 and/or second 210 tertiary catheters each may comprise a first 241, 251 and/or a second 242, 252 tertiary alignment portion. One first 241, 251 and/or one second 242, 252 tertiary alignment portion may be provided on each or one of the tertiary catheters 200, 210, e.g. located on a respective distal end portion 260, 270 or between the respective distal end portion 260, 270 and the respective proximal end portion 280, 290. The first 241, 251 and second 242, 252 tertiary alignment portion of a tertiary catheter 200, 210 may be abutting each other or may be spaced apart from each other.

The first tertiary alignment portion 241, 251 of one or both tertiary catheters 200, 210 may be provided so as to comprise a shape memory structure giving the first tertiary alignment portion 241, 251 a tendency (e.g. caused by material elasticity) to assume a first tertiary bent shape. Similarly, the second tertiary alignment portion 242, 252 of one or both tertiary catheters 200, 210 may be provided so as to comprise a shape memory structure giving the second tertiary alignment portion 242, 252 a tendency to assume a second tertiary bent shape. The first tertiary bent shape may correspond to (e.g. resemble, e.g. mate with) the first secondary bent shape. The second tertiary bent shape may correspond to the second secondary bent shape.

Accordingly, the first 200 and/or second 210 tertiary catheter may be aligned (e.g. be in a defined and predetermined position and rotational orientation relative to a respective secondary catheter 120, 130) with the first 120 and/or second 130 secondary catheter, respectively, when the first tertiary alignment portion 241, 251 of a tertiary catheter 200, 210 matches (e.g. mates) with a first secondary bent shape of a respective secondary catheter 120, 130. The first 200 and/or second 210 tertiary catheter may be aligned (e.g. be in a defined and predetermined position and rotational orientation relative to a respective secondary catheter 120, 130) with the first 120 and/or second 130 secondary catheter, respectively, when the second tertiary alignment portion 242, 252 of a tertiary catheter 200, 210 matches (e.g. mates) with a second secondary bent shape of a respective secondary catheter 120, 130. The first 241, 251 and/or the second 242, 252 tertiary alignment portion may be located on their respective tertiary catheter 200, 210 so that the alignment portion(s) of the respective tertiary catheter 200, 210 match with the first and/or second secondary bent shape (of a secondary catheter 200, 210), respectively, when the tertiary catheter 200, 210 is fully operatively exposed from the distal end portion 140, 150 of the respective secondary catheter 120, 130. The relative position and rotation of a tertiary catheter 200, 210 relative to a secondary catheter 120, 130 may be predetermined and defined more efficiently when both, the first and second tertiary bent shape of a tertiary catheter, mate with the first and second secondary bent shape of a respective secondary catheter 120, 130. However, the relative position and rotation of a tertiary catheter 200, 210 relative to a secondary catheter 120, 130 may be defined when there is only one of the tertiary bent shapes that mates with a corresponding secondary bent shape.

The tertiary alignment portion 241, 251 of one or both tertiary catheters 200, 210 may be flexible and may be provided so as to be flexible by a third flexing mechanism (not shown). The third flexing mechanism may be a shape memory structure as described above or may comprise any or all features of the first 191 and/or second 192 flexing mechanism, with the difference that the respective features refer to a tertiary catheter 200, 210 instead of a secondary catheter 120, 130.

The distal end portion 260, 270 of the first 200 and/or second 210 tertiary catheter may comprise a shape memory structure. The shape memory structure may give the distal end portions 260, 270 a tendency to assume oppositely orientated bow-shapes so that the distal ends 260, 270 of the tertiary catheters 200, 210 are substantially pointing towards each other when exposed, e.g. fully operationally exposed, from the secondary catheters 120, 130 (c.f. FIG. 1, FIG. 4 or FIG. 5c). Said oppositely oriented bow-shapes may serve to at least partially (e.g. fully) surround the circumferential tissue structure 10, e.g. in a generally circular or elliptical shape.

FIG. 5e schematically shows a single first tertiary catheter 200. As can be seen from FIG. 5e, the plane in which distal end portion 260 is extending in a bow shape may be substantially normal (i.e. may comprise an angle of substantially 90°) relative to the plane in which the second tertiary alignment portion 242 is extending, at least when it has assumed the second bent shape. However, there are also other angles possible between said planes, e.g. 80° to 90°, 30° to 60°, 70° to 80° or any other angle as appropriate for the use of the device. Although not shown in FIG. 5e, the same may apply at the same time for the second tertiary catheter 210. Further, it can be seen e.g. from FIG. 4c, that, when the first and second distal end portions 260, 270 of the first 200 and second 210 tertiary catheters are exposed, from the distal end portion 140, 150 of the first 120 and second 130 secondary catheters, the distal end portions 260, 270 of the first 200 and second 210 tertiary catheters each may substantially extend in a substantially same plane, that may be transverse to the longitudinal axis 90 of the primary catheter 70.

Figure 7A:
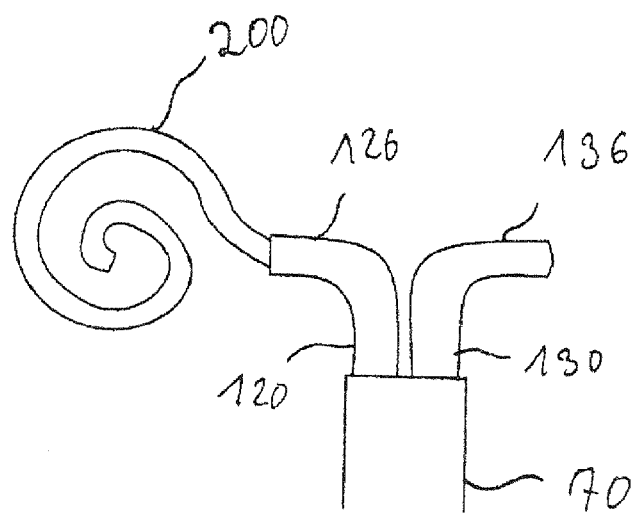
Figure 76:
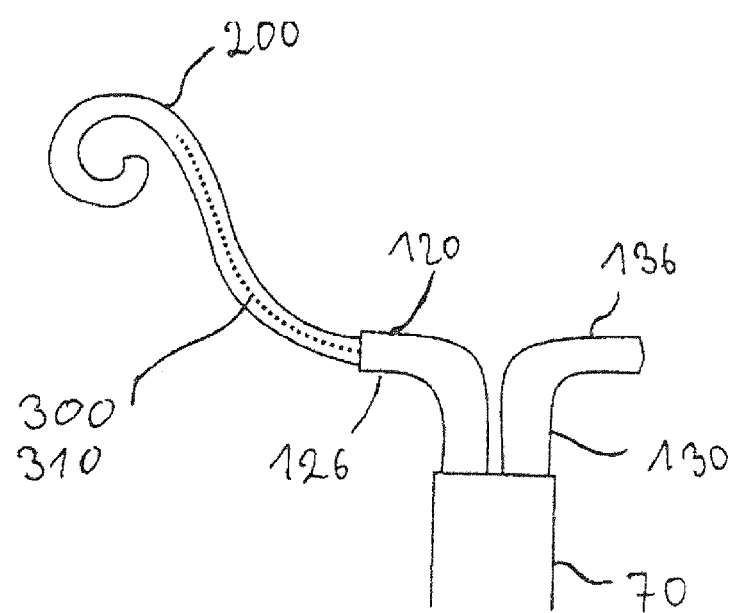
Figure 7C:
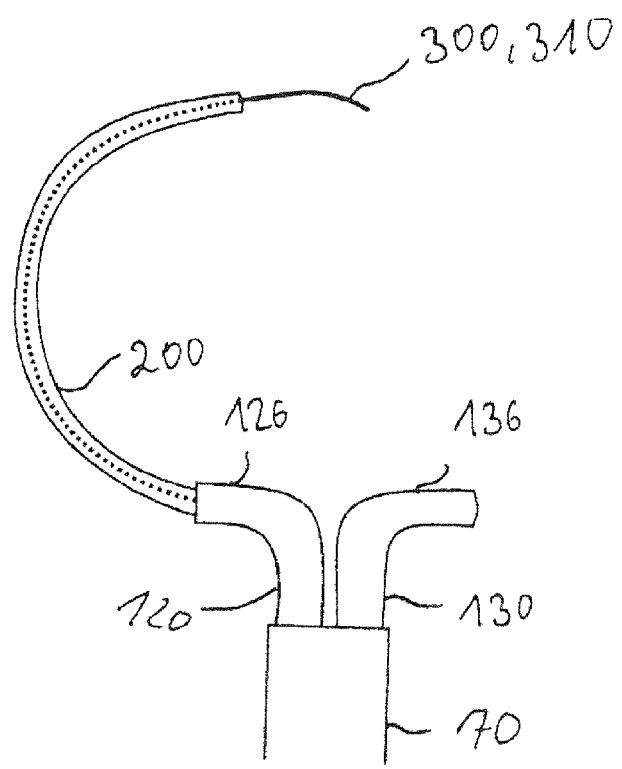

With further reference to FIGS. 7a, 7b and 7c, one and/or both tertiary catheters 200, 210 may also be at least partially folded, e.g. fully folded, at least when sheathed in a respective secondary catheter 120, 130. The distal end portion 260, 270 of the first 200 and/or second 210 tertiary catheter may comprise a shape memory structure giving it a tendency to assume a coil shape (e.g. a spiral shape, e.g. a pig tail shape, e.g. a helix shape, e.g. a screw shape), at least when forwarded from a distal end portion 140, 150 of a secondary catheter 120, 130. The coil shape may be a flat coil shape, i.e. the windings of the coil maybe located in substantially the same plane, or the coil shape may be a helix- and/or screw-type coil shape in which the windings of the coil may be arranged spaced along an axis so as to form a helix-type-structure. In this respect, the helix- or screw-type coil shape may have a constant pitch or variable pitch and/or a constant or variable radius of the windings. The distal end portion 260, 270 (e.g. the coil shape thereof) of the first 200 and/or second 210 tertiary catheter may be folded, e.g. packed, e.g. diametrically compressed (i.e. compressed in a radial direction of the coil shape) when sheathed in a respective secondary catheter 120, 130 and may unfold substantially at once (e.g. suddenly), when the folded or packed distal end portion 260, 270 is forwarded from a respective secondary catheter 120, 130. Accordingly, the distal end portion 260, 270 of the first 200 and/or second 210 tertiary catheter stray assume the coil shape when forwarded from a respective secondary catheter 120, 130 caused by the shape memory structure of the distal end portion 260, 270 of the first and/or second tertiary catheter 200, 210. The coil shape may comprise a plurality of windings, e.g. 1 to 2 windings, 1 to 5 windings, 3 to 7 windings or any other number of windings. In this respect, a winding may be a full winding (i.e. spanning an angle of 360°) and/or a partial winding (i.e. spanning an angle of less than 360°). A plurality of windings may comprise zero or more (e.g. one or more) full windings and/or zero or more (e.g. one or more) partial windings.

A longitudinal length of the first 200 and/or second 210 tertiary catheter may be longer than a longitudinal length of the first 120 and/or second 130 secondary catheter, respectively, so that a proximal end 280, 290 may be exposed from a proximal end 180, 190 of a respective secondary catheter 120, 130 to facilitate operation and relative movement of the catheters relative to each other. Also, a longitudinal length of each tertiary catheter 200, 210 may be longer than a longitudinal length of any secondary catheter 120, 130, whose length itself may be longer than a longitudinal length of a primary catheter 70.

Additionally, as shown in FIG. 4 and FIG. 5d, a front body tube 320 (e.g. front body catheter 320) may be provided relatively-moveable in an inner lumen 80 of primary catheter 70. The front body tube 320 may comprise a front body 330 which may be provided to serve several functions. The front body 330 may be provided to serve as a means for selectively closing or opening an inner lumen 80 of primary catheter 70. Therefore, the front body 330 may have a cross-sectional shape that is corresponding to a cross sectional shape (seen transverse to the longitudinal axis 90) of the inner lumen 80 of primary catheter 70 and a diameter that is substantially similar to the cross-sectional diameter of the inner lumen 80 of primary catheter 70 or slightly larger than that diameter to provide a press fitting. The front body 330 may be operable by the movement of the front body tube 320 along a longitudinal axis 90 of primary catheter 70, thereby moving front body 330 along the longitudinal axis 90 in a distal or proximal direction so as to open and close, respectively, the inner lumen 80 of primary catheter 70. Further, the front body 330 may serve to facilitate atraumatic insertion of the catheter member 1 by providing a curved or rounded front body 330. Therefore, the front body 330 may comprise a substantially round or curved or elliptical cross section when seen in a direction lateral to the longitudinal axis 90 of the primary catheter 70 (cf. e.g. FIG. 4 or FIG. 5d) so as to facilitate atraumatic insertion if front body 330 comes in contact with organic tissue. The front body 330 may comprise a through-opening and the front body tube 320 may comprise an inner lumen that is aligned with the through-opening of the front body 330 so that a guiding wire or the like may extend through the through-opening of the front body 330 and the inner lumen of the front body tube 320.

In the following, possible kinematic movements of the catheter member 1 will be described. As has been described above, primary catheter 70 may guide (e.g. sheath) a first 120 and a second 130 secondary catheter which are moveable relative thereto and which may optionally guide (e.g. sheath) a first 200 and a second 210 tertiary catheter, respectively, themselves, which are moveable relative thereto (and therefore also moveable relative to the primary catheter 70). In FIG. 1a, some kinematic possibilities of relative movement are schematically indicated by arrows 5. All kinematic actions of any catheter or wire or other object described herein above or below may optionally be selectively completely and fully reversible, e.g. some or all catheters that may be expanded and/or extended and/or moved and/or rotated and/or bent and/or flexed may selectively (e.g. on the discretion of a surgeon) be moved back and/or retracted and/or bent to their initial position/shape or any intermediate position/shape in between and be in a stable intermediate position.

The "strengths", i.e. the force or stress, with which a flexing mechanism 191, 192 or any shape memory structure described herein tries to induce (e.g. gives a tendency to assume) a predetermined shape upon a catheter described herein may be chosen so that the strength of one flexing mechanism 191, 192 or shape memory structure is higher than the sum of the strengths of all catheters that are guided by that catheter. This may result in a stable bent shape of said catheter that cannot be unintentionally substantially changed by relative movements of any other catheters that are guided by said catheter.

A typical aortic arch 340 of an adult human may have a radius of about 30 to 70 mm and define an angle of 90° to 270°. Therefore a secondary alignment portion 127, 137 may optionally have a radius ranging from approximately 30 to 70 mm, e.g. 30 to 50 mm, e.g. 40 to 45 mm and/or define an angle of 90° to 270°, e.g. 90° to 120°, 120° to 160°, 160° to 200°, 200° to 245° and/or 245° to 270°, when having assumed a second secondary bent shape. However, the radius or curvature of the secondary bent shape may also be provided to be suitable (e.g. custom made) to a specific heart of a patient, which size and geometry may have been determined by medical imaging techniques. While the catheter member I and its features have been described mainly with reference to a mitral valve 330 as circumferential tissue structure 10 and an aortic arch 340, the catheter member 1 may also be configured/designed with respect to other anatomic features or conditions. For example, the circumferential tissue structure 10 may be part or may be all of the tricuspid valve apparatus or any other valve and the curvature of the second secondary bent shape may be designed to mate with the curvature of a connection channel from the superior vena cava to the pulmonary artery of a mammal heart or may be designed to mate with any other curvature. Catheter member 1 may also be used to interact e.g. with a blood vessel, a gastric/digestive conduit/organ and/or a tracheal/pulmonary conduit. Catheter member 1 may also be used to interact e.g. with hard to reach parts of machinery or the like.

Figure 10:
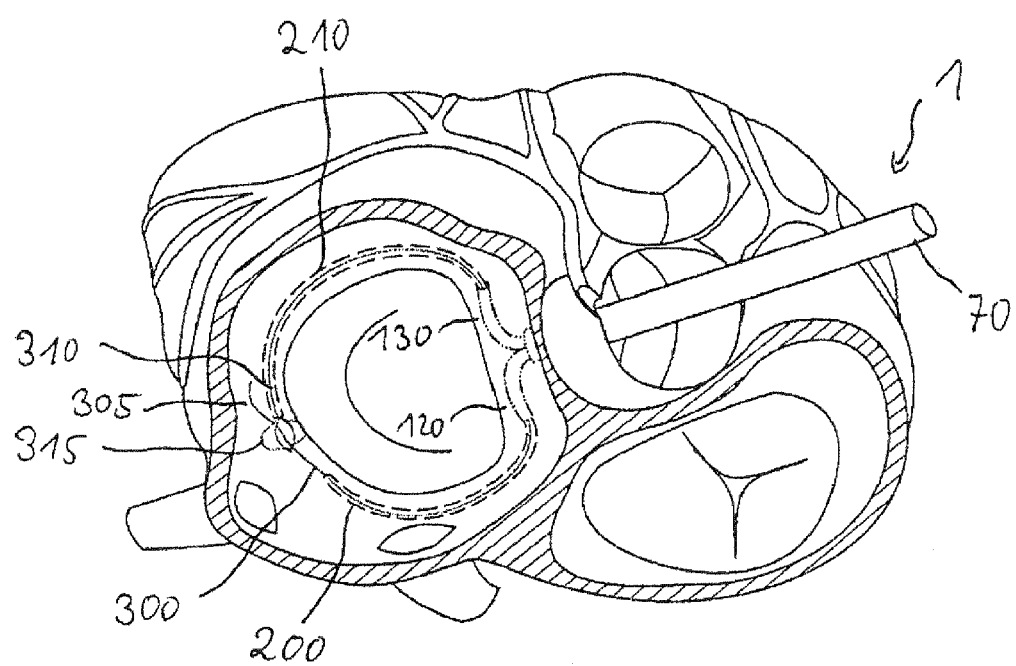

In the inner lumen 240 and 250 of the first 200 or the second 210 tertiary catheter there may be provided a wire 300 having a free distal end 305 wherein in the respective other tertiary catheter there may be provided a catching wire 310 having a distal catching component 315, as shown e.g. in FIG. 10 or 11. The wire 300 and/or the catching wire 310 may be moveable relative to their respective tertiary catheter 200, 210. The wire 300 and/or the catching wire 310 may be made from the same materials or may be made from different materials, e.g. from metal like steel or nitinol or from polymer like Kevlar or polypropylene (PP) or polystyrol (PS) or from a biodegradable material, e.g. a material that dissolves inside the human body in a substantially predetermined time.

The wire 300 and/or the catching wire 310 may be forwarded through the inner lumen 240, 250 of their respective first or second tertiary catheter 200, 210 to a distal end portion 260, 270 thereof and may be exposed therefrom.

The wire 300 and/or the catching wire 310 may also serve to give the first 200 and/or the second 210 tertiary catheter a shape, e.g. a predetermined shape, caused by material strength, material elasticity or a shape memory structure of the wire 300 and/or the catching wire 310. Accordingly, a wire 300 and/or a catching wire 310 may comprise material strength, material elasticity and/or a shape memory structure. The shape memory structure may give the wire 300 and/or the catching wire 310 a tendency to assume a bow shape (e.g. semi-circular shape, e.g. elliptical shape) or another shape. The bow shape may be a how shape having a radius that may be equal to or may be larger than a radius of an anatomic feature, e.g. of a circumferential tissue structure 10. When the wire 300 has a tendency to assume a bow shape, the catching wire 310 may have a tendency to assume a bow shape that is correspondingly oppositely oriented. In this respect, the respective bow shapes of the wire 300 and the catching wire 310 may form a circular shape.

With reference to FIGS. 7a to 7c, when a distal end portion 260, 270 of a first and/or second tertiary catheter 200, 210 is exposed from a respective secondary catheter 120, 130 and has assumed a coil shape as described above, the wire 300 and/or the catching wire 310 may be forwarded through a respective first and/or second tertiary catheter 200, 210 and may correspondingly unwind (e.g. further unfold, e.g. un-coil) the coil shape of the distal end portion 260, 270 of the first and/or second tertiary catheter 200, 210. This may cause the distal end portion 260, 270 of the first and/or second tertiary catheter 200, 210 to at least partially, e.g. fully, surround a structure, e.g. tissue structure 10. The unwinding of a coil shape as described above (e.g. by the wire 300 or catching wire 310) may allow atraumatic placement and/or insertion of the first and/or second tertiary catheter 200, 210 and/or wire 300 and/or catching wire 310 around a structure, e.g. tissue structure 10, as there may be substantially only be contact between a round winding of the coil shape and an anatomic feature.

The catching component 315 may be or comprise a catching basket 315 or a magnetic component or a hook or a snare or a lasso or any other device configured to catch and hold a free end 305 of wire 300. To facilitate catching and holding, the free end 305 of the wire 300 may comprise a barb or hook (not shown).

The catching component 315 may catch and hold the free end 305 when both are exposed from a distal end portion 260, 270 of their respective tertiary catheters 200, 210. The catching component 315 of the catching wire 310 may then be retracted back into the distal end portion of its (e.g. the second 210 or the first 200) tertiary catheter towards a proximal end portion 290 (or 280) thereof, dragging the free end 305 of the wire 300 (and thereby a part of the wire 300 as to well) into the, e.g. second, tertiary catheter 210 towards a proximal end portion 290 thereof. This may result in wire 300 at least partially (e.g. fully) surrounding an anatomic feature, e.g. tissue structure 10.

The circumference of inner lumen 80, 160, 170, 240, 250 of primary catheter member 70, secondary catheter(s) 120, 130 and/or tertiary catheter 200, 210 (and/or said catheters as a whole) may be selectively gas and liquid tight so that no gas or liquid can diffuse out from the inner lumen or can diffuse into the inner lumen. However, any one or all of said inner lumina may also not be liquid or gas tight and allow trolled outwards diffusion of matter, e.g. contrast dye or other substances enabling specific visualization or a drug, from an inner lumen to the exterior of catheter member 1, e.g. for treatment or other purposes, or controlled inwards diffusion, e.g. to take samples of a plasmid coding for a protein.

The catheter member 1 as disclosed herein may also be used in combination with a medical implant. The first 200 and/or secondary 210 tertiary catheter (and/or the first 120 and/or second 130 secondary catheter) may accordingly be configured so as to deliver an implant to be circumferential tissue structure 10. The implant can be a stent or stent-graft like structure, a balloon or similar actively inflatable member, a foam/hydrogel covered or otherwise passively expandable member. The implant can be anchored by its shape, or by additional anchoring components or through interaction with another device, e.g. inserted by a different delivery catheter; the implant may e.g. be a replacement heart valve that can be delivered within be tissue structure 10 (e.g. between the native mitral or tricuspid leaflets).

In the following, a method of using a catheter member 1 to catch a tissue structure 10 will be described in more detail with reference to FIGS. 8 to 12. Any feature of a catheter member 1 that is described directly or indirectly in any method step is intended to also be applicable for the catheter member "device" and any feature or functionality that is described relating to the catheter member "device" may also be applicable as a method step of a method of using the catheter member 1. In addition, other devices than those described herein may be used to perform the method steps described herein.

FIGS. 8 to 12 show schematic views of the human heart with a view from the left atrial chamber 350 onto the mitral valve 360 which may be or may comprise circumferential tissue structure 10 (see also FIG. 2). The catheter member 1 can be seen with a distal end portion 100 of the primary catheter 70 being positioned in the ventricular chamber 370 (therefore, in FIGS. 8 to 12 "under" mitral valve 360, c.f. FIG. 2). The catheter member 1 is inserted via the aortic arch 340 so that the distal end portion 100 of the primary catheter 70 may be located adjacent to the circumferential tissue structure 10. The first 120 and second 130 secondary catheters, which may be guided by the primary catheter 70 (which may be flexible), may be arranged as such relative to the aortic arch 340, that the second flexing mechanism 192 may cause the secondary alignment portions 127, 137 to assume their respective secondary bent shape. This may result in the secondary alignment portions of secondary catheters 120, 130 being auto-aligned and/or auto-oriented with the aortic arch 340, resulting in a corresponding auto-alignment or auto-orientation of the distal end portions 140. 150 of the first 120 and second 130 secondary catheters, as described above.

Figure 8:
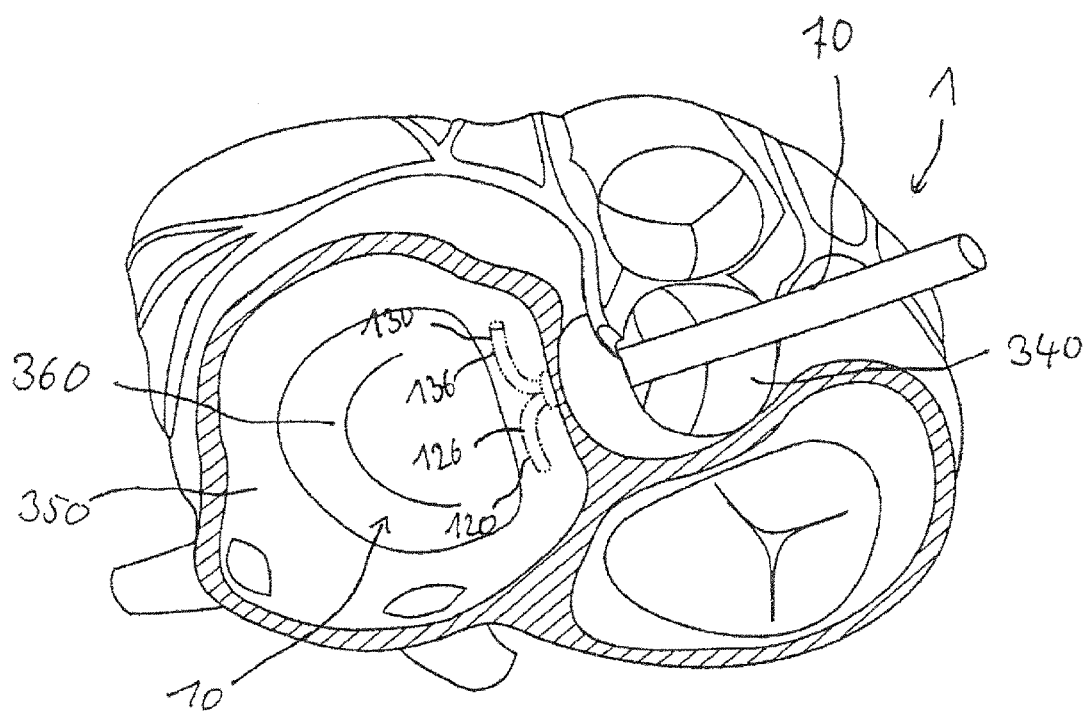
FIGS. 8 to 12 show various exemplary method steps of a method for using a catheter member.

In FIG. 8 it can be seen that the first and second secondary catheters 120, 130 are exposed from a distal end portion 100 of primary catheter 70. Arm portions 126, 136 are extending in substantially opposite directions transverse to the longitudinal axis 90 (not shown in FIG. 8) of primary catheter 70 with a corresponding arm length (i.e. the length of rectilinear extension) of approximately 4 or more mm (as described above the arm length nay however be longer or shorter) caused by the first flexing mechanism 191.

Figure 9:
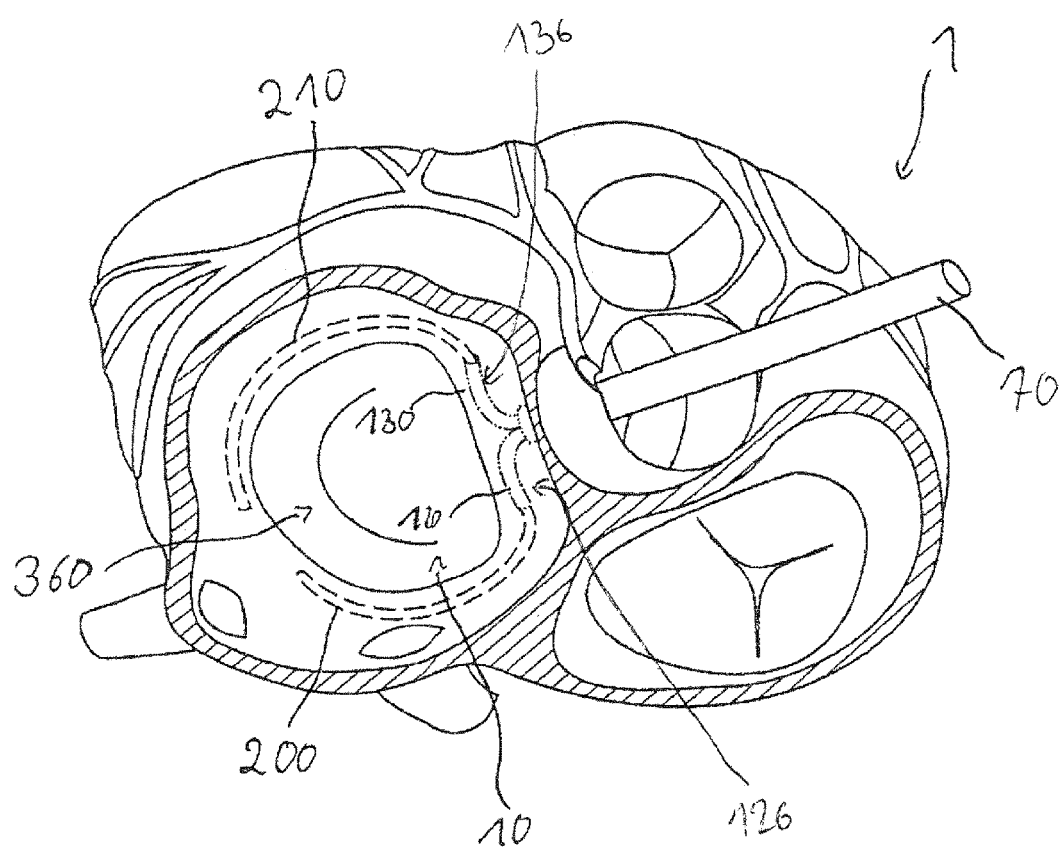

FIG. 9 shows the first 210 and second 220 tertiary catheters being exposed from a distal end portion 140, 150 of the first 120 and second 130 secondary catheters, respectively, so as to expand substantially in oppositely-oriented bow shapes towards each other to surround a circumference of mitral valve 360 (or any other circumferential tissue structure 10).

FIG. 10 shows the exposed free end 305 of wire 300 caught by the catching component 315 of catching wire 310. Here, catching component 315 is a catching basket. Wire 300 and catching wire 310 are forwarded through the inner lumina 240, 250 of first 200 and second 210 tertiary catheters, respectively, from a proximal end portion 280, 290 (e.g. from the outside of a body) of the first 200 and second 210 tertiary catheters, respectively, to be exposed from distal end portions 260, 270 thereof, so that the free end 305 of wire 300 may be reliably caught by the catching component 315 of catching wire 310.

FIG. 11 is similar to FIG. 10 but shows a different/alternative arrangement of the second secondary catheter 130 and the second tertiary catheter 210. Here, second secondary catheter 130 and second tertiary catheter 210 have shape so as to be substantially parallel to a longitudinal axis 90 (not shown in FIG. 11) of primary catheter 70 and first secondary catheter 120 and first tertiary catheter 200 comprise an arm portion 126 as described above with reference to e.g. FIG. 10 that is substantially transverse to longitudinal axis 90 or primary catheter 70. This results in catheter member 1 only partially surrounding a circumferential structure of a mitral valve 360 or other structure. As can be seen from FIG. 11, arm portion 126 is provided substantially transverse to longitudinal axis 90 of primary catheter 70, while arm portion 136 is provided substantially parallel to longitudinal axis 90. Further, as can be seen in FIG. 11, in order for the catching component 315 to reliably catch the free end 305 of the wire 300, it may not be necessary that distal end portions 260, 270 of first and/or second tertiary catheters 200, 210, respectively, are oriented in a certain manner or angle relative to each other nor is it necessary that they touch or abut each other.

Figure 12:
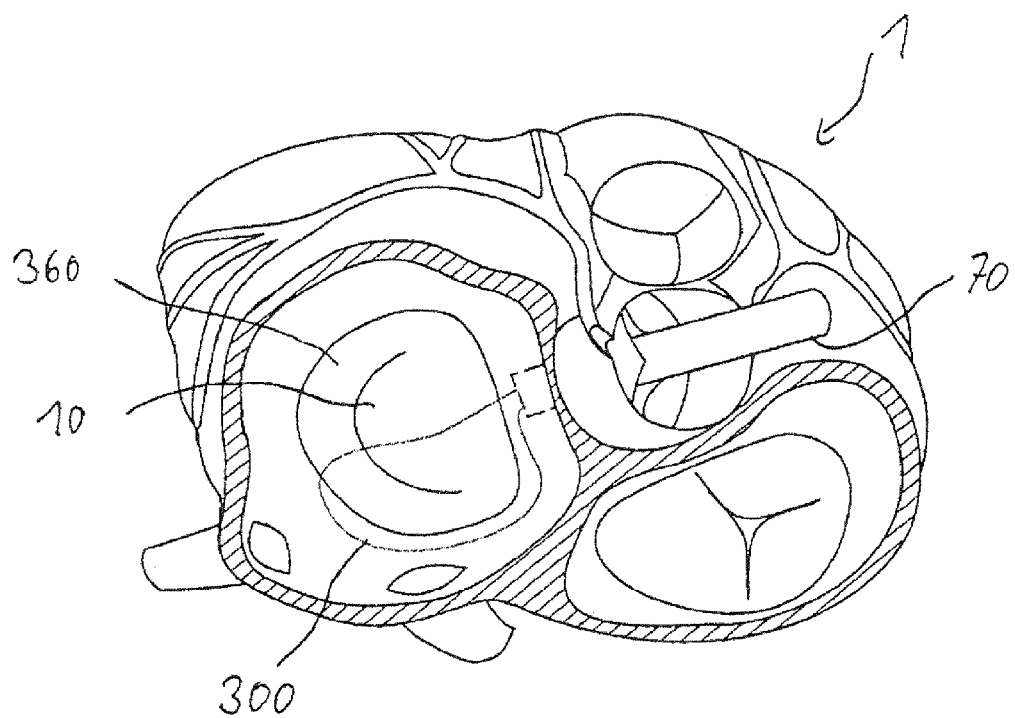

FIG. 12 shows a further step of a method for using catheter member 1. The arrangement of the catheter member 1 of FIG. 12 is based on the one shown in FIG. 11, but all principles described in FIG. 12 or with reference to FIG. 12 may also be applicable to the arrangement shown in FIG. 10. In FIG. 12, the catching wire 310 with the free end 305 of the wire 300 being caught in catching component 315 is retracted into inner lumen 250 of second tertiary catheter 210, thereby dragging the wire 300 around part of the mitral valve 360 and into the inner lumen 250 of the second tertiary catheter 210 as well. Further, in FIG. 12, the first and second tertiary catheters 200, 210 and the first and second secondary catheters 120, 130 are retracted into the inner lumen 80 of primary catheter 70. This may result in the wire 300 surrounding a circumference of a mitral valve 360 (in FIG. 12 partially, however when using a catheter member 1 as shown FIG. 10, fully).

The wire 300 extending around the circumferential tissue structure of mitral valve 360 may enable further treatment of the valve, fixation of other catheters or artificial heart valves or the like. For example, it may be used to fix an artificial heart valve as described in PCT Publication No. WO 2012/004679, the entire contents of which are hereby incorporated by reference and/or it may be used to serve as an outer member or for placing an outer member or other circumferential implant support structure or the like as described in PCT application No. PCT/EP2012/067801, the entire contents, of which are hereby incorporated by reference.

While the above method may have been described based on a mitral valve 360 for better illustration of general principles, it may generally relate surrounding any tissue structure 10 to and even surrounding any circumferential structure, e.g. hard to reach parts of machinery or other circumferential structures in confined spaces.

With further reference to FIG. 13, the catheter member 1 may be configured to surround the circumferential tissue structure 10 from a side of the circumferential tissue structure 10 that is opposite to the aortic arch 340. Accordingly, the distal end portion 100 of the primary catheter 70 may be placed on the far side of the circumferential tissue structure 10 with reference to the aortic arch 340. Accordingly, first 120 and/or second 130 secondary catheter and/or first 200 and/or second 210 tertiary catheter may be configured to surround the tissue structure 10 (at least partially, e.g. completely) starting from a location on the circumferential tissue structure 10 that is located opposite of aortic arch 340. In this respect, catheter member 1 may be configured to surround tissue structure 10 from any location with respect to the aortic arch 340.

Figure 14C:
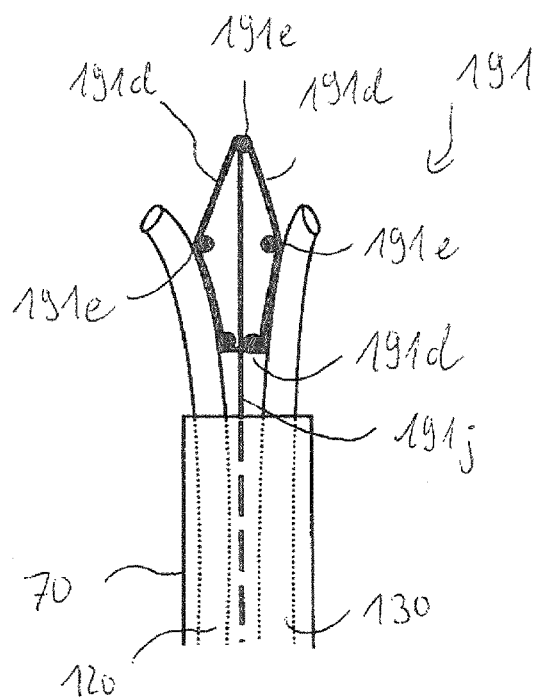

FIGS. 14a to 14f show further variations of the first flexing mechanism (also see FIG. 6). According to FIGS. 14a and 14b, the first flexing mechanism 191 may be implemented by (and, accordingly, comprise) a (e.g. one) link member 191d and two joint members 191e. Each joint member 191c may be provided on the distal end portion 140, 150 of the first 120 and second 130 secondary catheters (e.g. on the distal end thereof or in an area close thereto), respectively. The link member 191d may be a stiff or rigid or flexible longitudinal element comprising two longitudinal end portions that each may be connected with one of the two joint members 191e. The connection between a joint member 191e and the link member 191d may be configured to allow rotational movement between the link member 191d and the first 120 or second 130 secondary catheter. In this respect, a joint member 191e may be implemented as a hinge between a longitudinal end of the link member 191d and the first 120 or second 130 secondary catheter. Accordingly, as shown in FIG. 14a, when the first 120 and second 130 secondary catheters are sheathed in the inner lumen 80 of the primary catheter 70, a longitudinal axis of the link member 191d may substantially be aligned with the longitudinal axis 90 of the primary catheter 70, wherein the distal end portions 140, 150 of the first and second secondary catheters 120, 130 have a distance along longitudinal axis 90 of the primary catheter 70 from each other that corresponds to the distance of the two joint members 191e (and therefore also corresponds to the longitudinal length of link member 191d). That is, the distal end portions 140, 150 of the first and second secondary catheters 120, 130 may have a distance to each other in a direction along the longitudinal axis 90 of the primary catheter 70 (and, accordingly, may also have a distance along longitudinal axes 125, 135 of the secondary catheters 120, 130). When, as shown in FIG. 14b, the first and second secondary catheters 120, 130, that have a distance from each other corresponding to a length of the link member 191d while sheathed in the primary catheter 70, are forwarded from the distal end portion 100 of the primary catheter 70, and then the first and/or second secondary catheters 120, 130 are/is moved so that the axial distance (axial with respect to the longitudinal axis 90 of primary catheter 70) between the distal end portion 140 of the first secondary catheter 120 and the distal end portion 150 of second secondary catheter 130 is changed (e.g. reduced), the link member 191d, that is rotatably connected to the first and second secondary catheters 120, 130 via the joint members 191e, will cause a lateral deflection (with respect to longitudinal axis 90 of primary catheter 70) of the distal end portions 140, 150 of the secondary catheters 120, 130. Accordingly, the arm portions 126, 136 are formed by the interaction of link member 191d and joint members 191e (constituting first flexing mechanism 191 as shown in FIGS. 14a and 14b) with the distal end portions 140, 150 of the first and second secondary catheters 120, 130.

Figure 14D:
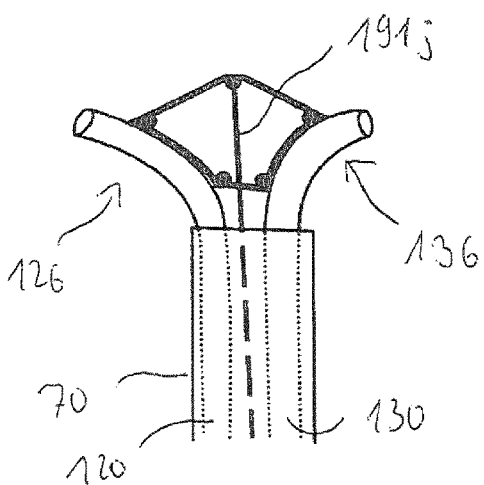

FIGS. 14c and 14d show a further variation of the first flexing mechanism 191 comprising link members 191d and joint members 191e. Here, a first link member 191d is connected with the first secondary catheter 120 (e.g. the distal end portion 140 thereof) via a first joint member 191e, and a second link member 191d is connected with the second secondary catheter 130 (e.g. distal end portion 150 thereof) via a second joint member 191e. Further, the end portions of the first and second link members 191d that are opposite to the respective end portions of the first and second link members 191d, that are connected with the first and second, respectively, secondary catheters 120, 130, are rotatably interconnected by a third joint member 191e. Further, a longitudinal operation member 191j may be connected with one (longitudinal) end thereof to the first link member, the second link member 191d and/or the third joint member 191e (as shown in FIGS. 14c and 14d). The operation member 191j may be (partially) sheathed in the inner lumen 80 of the primary catheter 70 and may be moveable relative thereto. The other longitudinal end of the operation member 191j may extend to the proximal end 110 of the primary catheter 70 and may there be exposed to the outside to be operable, e.g. by a surgeon or by a driving mechanism or the like.

As shown in FIG. 14d, operating the operation member 191j may move the third joint member 191e (or the first or second link member) in a longitudinal direction of the primary catheter 70 and may accordingly flex the first and second catheter members 120, 130 (e.g. the distal end portions 140, 150 thereof) via the first and second link members 191d and the first, second and third joint members 191e, whereby the distal end portion 100 of the primary catheter 70 may serve as a "counter" support for flexing the secondary catheters. In addition or alternatively, optionally, as shown in FIGS. 14c and 14d, further link members 191d and joint members 191e may also be provided. For example, a fourth link member 191e may be connected to the first and second secondary catheters 120, 130 via fourth and fifth joint members 191e (that may provide a rotatable connection or a rigid connection) that are provided spaced in a proximal direction from the first and second joint members 191e. Accordingly, the fourth link member 191e may serve as a "counter" support when flexing the first and second secondary catheters 120, 130 to form arm portions 126, 136. Optionally, also a fifth link member 191e may be provided connecting between first joint member 191e and fourth joint member 191c (connecting first secondary catheter 120 and the fifth link member) and/or a sixth link member 191e may be provided connecting between second joint member 191e and fifth joint member 191e (connecting second secondary catheter 130 and the fifth link member) in order to further improve efficiency of the first flexing mechanism 191.

Figure 14E:
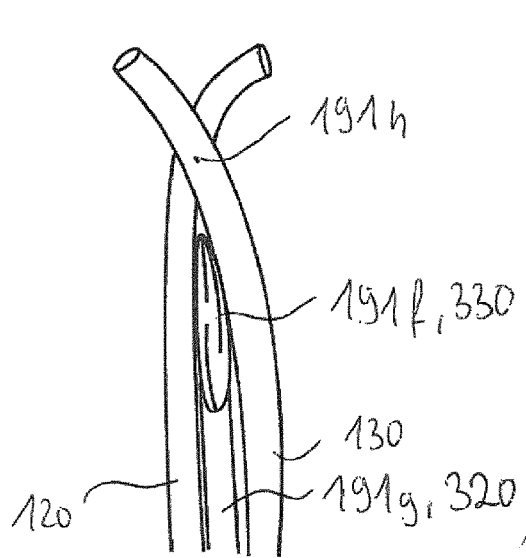
Figure 14F:
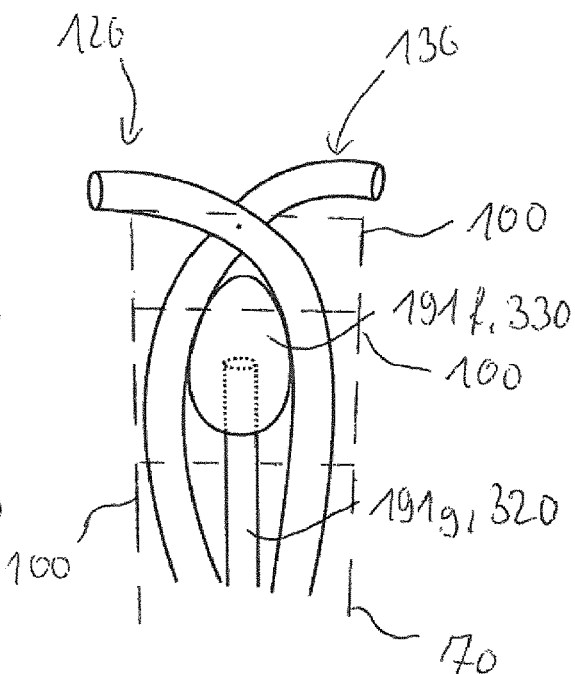

A further variation of first flexing mechanism 191 is shown in FIGS. 14e and 14f. Here, the first and second secondary catheters 120, 130 may be connected via a hinge member 191h. The hinge member 191h may connect the distal end portions 140, 150 of the secondary catheters 120, 130 or may connect portions having a longitudinal distance (along longitudinal axes 125, 135) from the distal end portions 140, 150. The hinge member 191h may be configured to enable rotation of the secondary catheters 120, 130 relative to each other along a rational axis that may be substantially perpendicular to the longitudinal axes 125, 135 of the secondary catheters. Besides the hinge member 191h, the first flexing mechanism 191 according to a variation may also comprise an inflatable/deflatable member 191f (in the following designated as "inflatable member") and an inflatable member catheter 191g that is connected to the inflatable member 191f. The inflatable member catheter 191g and the inflatable member 191f may be (at least partially) sheathed in the inner lumen 80 of the primary catheter 70. The inflatable member catheter 191g and the inflatable member 191f may be (at least partially) longitudinally moveable relative to the primary catheter 70. The inflatable member 191f may have a deflated state characterized by a reduced diameter in a direction perpendicular to the longitudinal axis 90 of the primary catheter 70 and may have an inflated state characterized by an enlarged diameter in a direction perpendicular to the longitudinal axis 90 of the primary catheter 70. When the inflatable member 191f is sheathed in the primary catheter 70, it may be in its deflated state. In order to flex the distal end portions 140, 150 of the secondary catheters 120, 130, said distal end portions (that may be connected by hinge member 191h) may be forwarded and exposed from the primary catheter 70. Then, the inflatable member 191f may be positioned by the inflatable member catheter 191g at a position proximally spaced from the hinge member 191h. Then, the inflatable member 191f may be brought to its inflated state so that it applies an outwards force on the first and second secondary catheters, resulting in a rotation thereof around hinge member 191h. As a consequence, the distal end portions (or parts thereof) 140, 150 of the secondary catheters 120, 130 that are located distally from the hinge member 191h may be moved outwardly in a radial direction (in respect to e.g. longitudinal axis 90 of primary catheter 70) so as to form arm portions 126, 136. The inflatable member 191f may be implemented as a balloon or a membrane to which and/or from which a substance such as a gas or liquid may be supplied in order to realize the inflated and/or deflated state or any intermediate state. Accordingly, the shape and position of arm portions 126, 136 may be controlled via the inflated/deflated/intermediate state of the inflatable member 191f and/or via the distance of the inflatable member 191f to the hinge member 191h (which may be adjusted by moving the inflatable member 191f and the secondary catheters 120, 130 relative to each other, e.g. via the inflatable m member catheter 191g). It is noted that the inflatable member 191f may also or alternatively be implemented as a shape memory structure and/or an elastic structure that may have a reduced and an enlarged diameter state that are realized without supplying a liquid or gas or the like. In this respect, the inflatable member 191f may be in a compressed state having a reduced diameter when sheathed in the inner lumen 80 of primary catheter 70, and may be in an uncompressed state having an enlarged diameter when forwarded from, the inner lumen 80 of primary catheter 70. The uncompressed state may, for example, be achieved by material elasticity that may enlarge the diameter once the constraint posed by the inner lumen 80 of primary catheter 70 is removed by exposing inflatable member 191f from the primary catheter 70. It is further noted that inflatable member 191f and inflatable member catheter 191g may also at the same time serve as blunt front body 330 and front body tube 320, respectively. In this respect, the inflatable member may close the proximal end of primary catheter 70 (e.g. when having an "intermediate" or reduced diameter state as described above and being in a position that is distal from the hinge member 191h), e.g. when catheter member 1 is forwarded to a tissue structure), and may then serve as first flexing mechanism 191 (e.g. when having the enlarged diameter state and being moved to position proximal from the hinge member 191h). In this respect, inflatable member 191f may be configured so that it may pass hinge member 191h in a longitudinal direction of primary catheter 70, at least when it is in a deflated/reduced diameter state).

With respect to FIGS. 15a to FIG. 15e, a variation of a catheter member 1 and a method of using the same are described. It is noted that all features described herein (such as first and/or second flexing mechanism 191, 192, arm portions, etc.) may apply also to the catheter member 1 and the method described with reference to FIGS. 15a to 15e, and accordingly, features not yet described above will be described with reference to FIGS. 15a to 15e. Primary catheter 70 may comprise an opening 75 that may be located in the distal end portion 100 thereof or between the proximal end portion 110 and the distal end portion 100 thereof (e.g. close to the distal end portion 100). The opening 75 may be connecting the or one inner lumen 80 of primary catheter 70 with the surroundings/outside of primary catheter member 70. In this respect, the opening may be open in a lateral direction with respect to longitudinal axis 90 of primary catheter 70 or it may define an angle thereto (e.g. between 30 to 80 degree, e.g. 40 to 60 degree, e.g. substantially 45 degree, wherein the angle is counted from perpendicular direction with respect to longitudinal axis 90 in a direction towards the distal end (portion) of primary catheter 70).

The variation of catheter member 1 that is shown in FIGS. 15a to 15e may be provided with a catching mechanism 450. The catching mechanism 450 may be configured to be moveable with respect to primary catheter 70 in a longitudinally proximal and/or distal direction thereof. The catching mechanism 450 may be forwarded (and/or retracted) from the or an (e.g. a separate) inner lumen 80 of primary catheter 70 via opening 75 to the outside of primary catheter 70 to be exposed. The catching mechanism 450 or a part thereof (see below) may also be moveable relative to the primary catheter 70 when the catching mechanism 450 is forwarded and exposed from primary catheter 70.

The catching mechanism 450 may be configured to catch one or more (e.g. two) wires and/or catheters (such as the first and/or second tertiary catheter) or the like. For example, the catching mechanism 450 may be configured to catch wire 300 and/or catching wire 310 (that may be provided with or without a distal catching component 315), e.g. the distal ends thereof. The catching mechanism 450 may also be configured to catch one or more (e.g. both) tertiary catheters 200, 210, e.g. the distal end portions 260, 270 thereof. The catching mechanism 450 may be configured to catch any one or two wire(s) or catheter(s) described herein. The catching to mechanism 450 may also be configured to catch catching mechanism 315, which may be used to catch free distal end 305 of wire 300 as described above. As indicated, catching wire 310 may also be provided without catching, component 315, and the catching mechanism 450 may accordingly catch the distal ends of wire 300 and catching wire 310 that may or may not comprise a catching component 315 when it gets caught by catching mechanism 450. (In this respect, it is noted that wire 300 and catching wire 310 herein may also be designated as first wire 300 and second wire 310 (corresponding to the catching wire 310 that is provided without a catching component 315), respectively, herein).

The catching mechanism 450 may be configured to selectively and controllably move the caught wire(s) and/or catheter(s) and/or components with respect to primary catheter 70. This may for example serve to move wire 300 (that may be partially or fully surrounding an anatomic feature as described above) and/or wire 315 and/or tertiary catheters 200, 210 relative to primary catheter 70 and accordingly also relative to said anatomic feature (e.g. tissue structure 10) as it is described in more detail further below.

The catching mechanism 450 may comprise a catching device configured to catch wires, catheters or other elements such, as catching component 315). Said catching device may be or comprise a catching basket 470 (as shown) and/or a magnetic component and/or a hook and/or a snare and/or a lasso car a combination thereof.

The catching mechanism 450 may optionally comprise a catching mechanism controller 460 (hereinafter referred to as controller 460). The controller 460 may be configured to control the position of wires, catheters or other elements/components that are caught with/by the catching mechanism 450 (e.g. the catching device thereof) as described in further detail below.

According to an exemplary variation, the controller 460 may comprise a control catheter 480 that may comprise one or more inner lumen and may be moveable relative to the primary catheter 70 while being sheathed therein (e.g. sheathed in inner lumen 80 or a separate inner lumen of primary catheter 70). A proximal end of control catheter 480 may be exposed from the proximal end portion 110 of primary catheter 70 to be operable. Operating the control catheter 480 may include moving the control catheter 480 relative to the primary catheter 70 in a longitudinal direction thereof.

A control wire 490 may be sheathed in the control catheter 480 and may be moveable relative thereto. A distal end of the control wire 490 may be connected to the catching device, that is to catching basket 470 (as shown) or a magnetic component or a hook or a snare or a lasso or the like. The proximal end of control wire 490 may be exposed from the proximal end portion 110 of primary catheter 70 to be operable. Accordingly, by operating be control wire 490, the control wire 490 and the catching device (e.g. catching basket 470 as shown) connected thereto may be moved relative to control catheter 480.

For example, when the catching mechanism 450 is implemented as a catching basket 470 (e.g. made from elastic metal or plastic wire or a shape-memory material or the like), the controller 460 may be implemented as a control wire 490 that is sheathed in a control catheter 480. The catching basket 470, which may be provided in a compressed/folded state inside the control catheter 480, may be moved proximally and/or distally with respect to the opening 75 of the primary catheter 70 by moving control catheter 480 and/or control wire 490 relative to primary catheter 70. Accordingly, the catching basket 470 may be forwarded to the outside of primary catheter 70 via opening 75 (and control catheter 480) or may be retracted therethrough from the outside into control catheter 480 and/or primary catheter 70 by operating control wire 490 and control catheter 480.

When the catching basket 470 is exposed from the control catheter 480 (and primary catheter 70), it may be unfolded from its compressed/folded state, e.g. using its elastic and/or shape-memory properties. When the catching basket 470 is retracted into the control catheter 480, it may be compressed/folded to assume its compressed/folded state, e.g. via the geometric constraint that is formed by control catheter 470 (e.g. by the distal end opening of a lumen thereof). When said catching basket 470 is forwarded form the control catheter 480 and the primary catheter 70 (that is, when it is exposed to the surroundings of catheter member 1), it may be moveable relative to the primary catheter 70 while being exposed to the outside of primary catheter 70 and while e.g. being in its unfolded/decompressed state. The catching device (e.g. catching basket 470 as exemplified above) may be moved relative to primary catheter 70 while the position of control catheter 480 remains substantially constant with respect to primary catheter 70 (that is, the catching device may be moved by moving control wire 490). However, in addition or as an alternative, the catching device may also be moved by moving control catheter 480 and control wire 490 correspondingly so that the position of the catching device remains substantially constant with respect to control catheter 480, hut the positions of catching device and control catheter 480 are changed with respect to primary catheter 70.

When the catching mechanism 450 comprises a magnetic component as catching device (not shown), the controller 460 may optionally further comprise an electrical wire that may be connected with the magnetic component and an external power source (e.g. provided on the proximal end portion 110 of the primary catheter 70, e.g. spaced from a patient), in order to provide a current/bias to the magnetic component to increase a magnetic force of the magnetic component. Additionally or optionally, when the controller 460 is electrically conductive, it may be used directly to transmit a current/voltage to the magnetic component without the need for a separate or the like. The magnetic component is not necessarily implemented as an electromagnet, but may also be implemented as a conventional magnet such as a neodymium-iron-boron magnet or a permanent iron-magnet or the like.

In the following, an exemplary method for using, a catheter member 1 having a catching mechanism 450 as described above will be explained. It is intended that features that are described relating to the catheter "device" may also be applicable as method steps and that features described relating to method steps may also be applicable to the catheter "device".

Figure 13A:
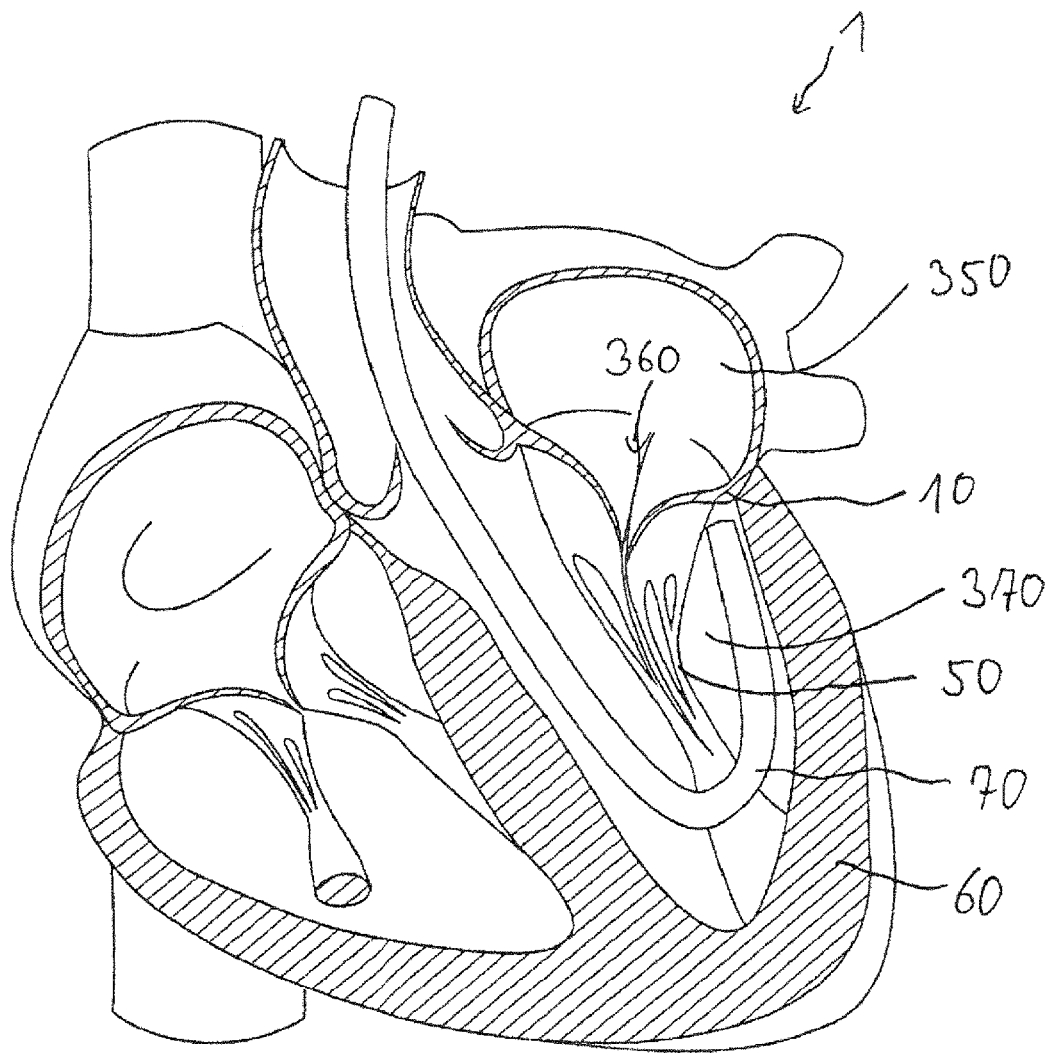
FIGS. 13a and 13b show a catheter member according to a variation.
Figure 13B:
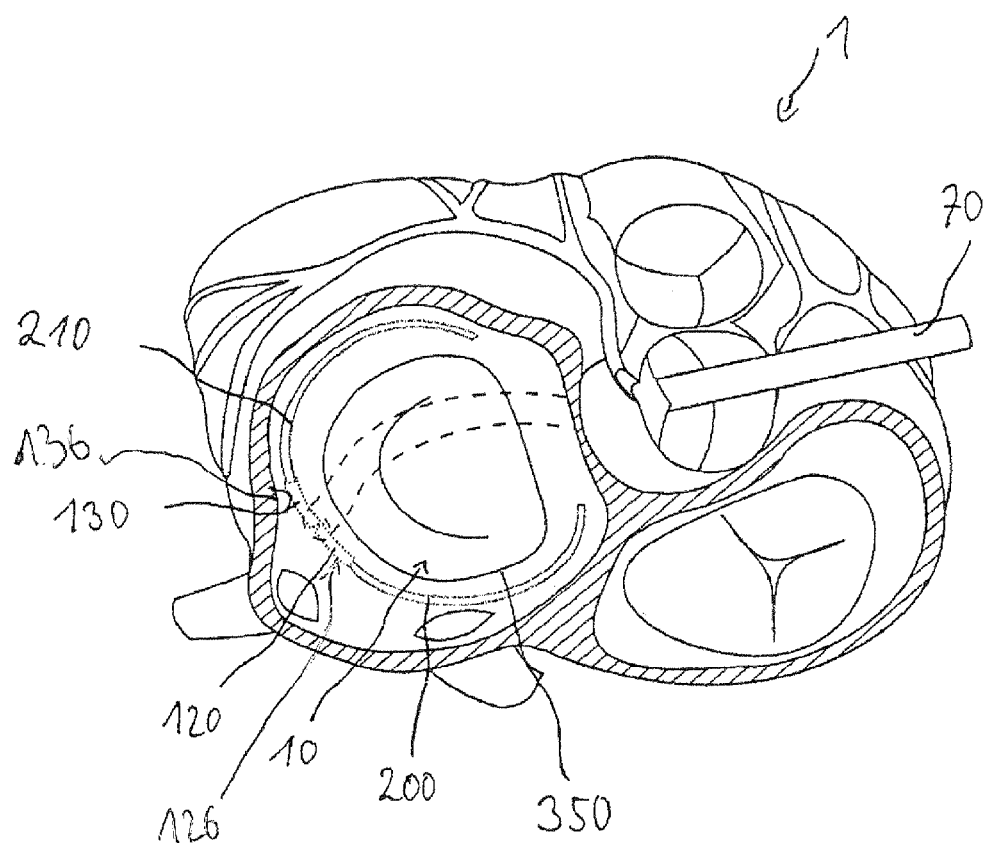
Figure 15A:
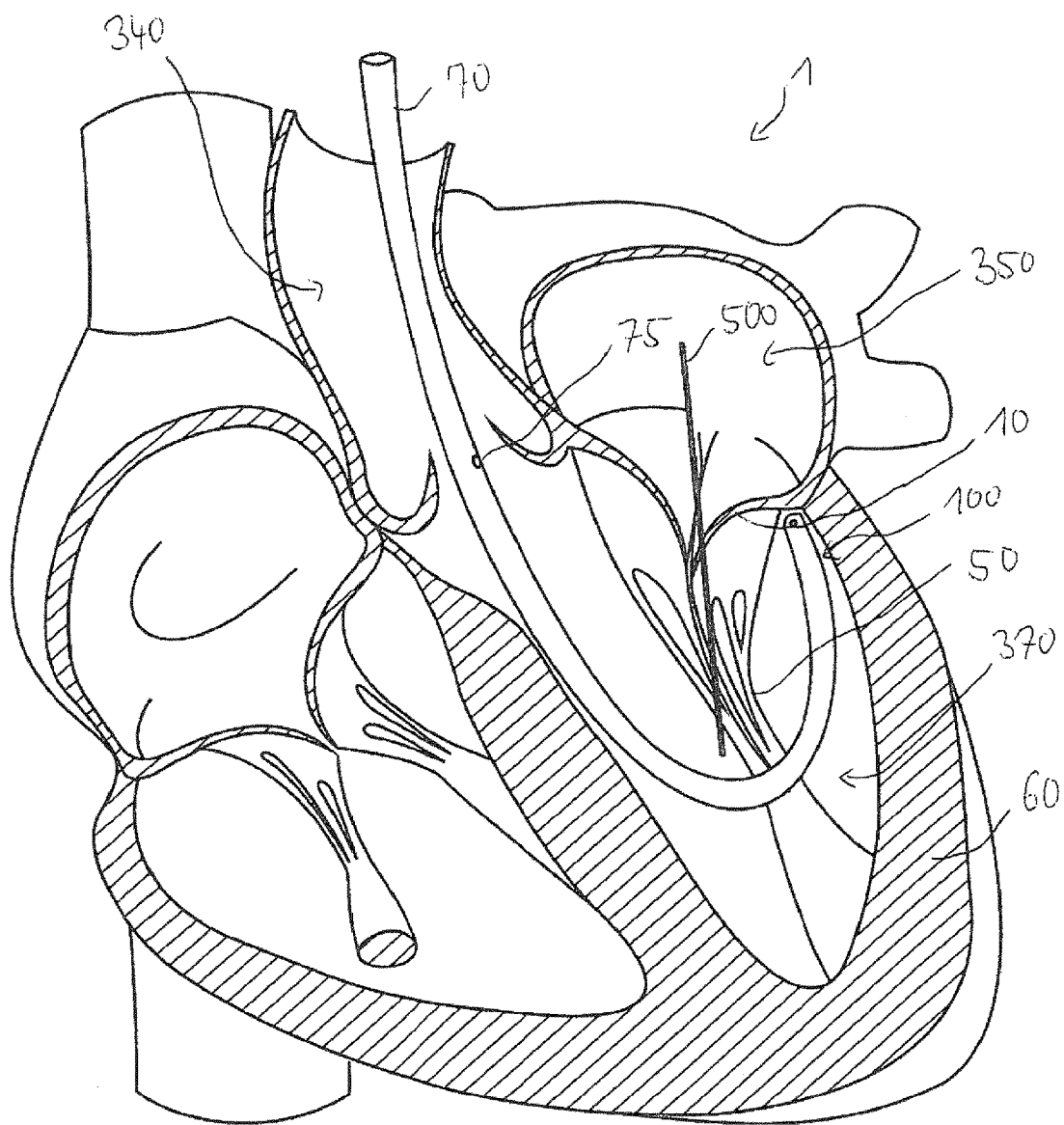
FIGS. 15a to 15e show a catheter member and a method of using thereof according to a variation.

FIG. 15*a* shows a view of a section of a human heart that is substantially similar to the views shown in FIG. 12 or FIG. 13*a*. Here, catheter member 1 has an opening 75 as described above provided with primary catheter 70. Catheter member 1 is forwarded through the aortic arch 340 so that the distal end portion 100 of primary catheter 70 extends into the ventricular chamber 370 and is placed on a side of tissue structure 10 that is substantially opposite to aortic arch 340

(e.g. using an alignment portion and a flexing mechanism as described above). The opening 75 is provided on primary catheter 70 so that it is generally located on the same axial level as the distal end portion 100 of the primary catheter 70 when the primary catheter 70 is in its operational position. The axial level may be defined with respect to an axis 500 connecting mitral and ventricular chambers 350, 370 via valve annulus 30/connection channel wall structure (e.g. a center point thereof). Further, the opening 75 is radially provided on primary catheter 70 so that the opening 75 is generally facing distal end portion 100 thereof. It is to be noted that "generally on the same level" may refer to positions slightly proximally or distally spaced (e.g. equal to or less than 0.01 or 0.1 or 0.3 or 0.5 or 1 or 2 or 3 or 4 or 5 cm or 7 cm or a different distance proximally or distally spaced. wherein the distance is counted along longitudinal axis 90 of primary catheter 70) on primary catheter 70 from the level of distal end portion 100 with respect to axis 500.

Figure 15B:
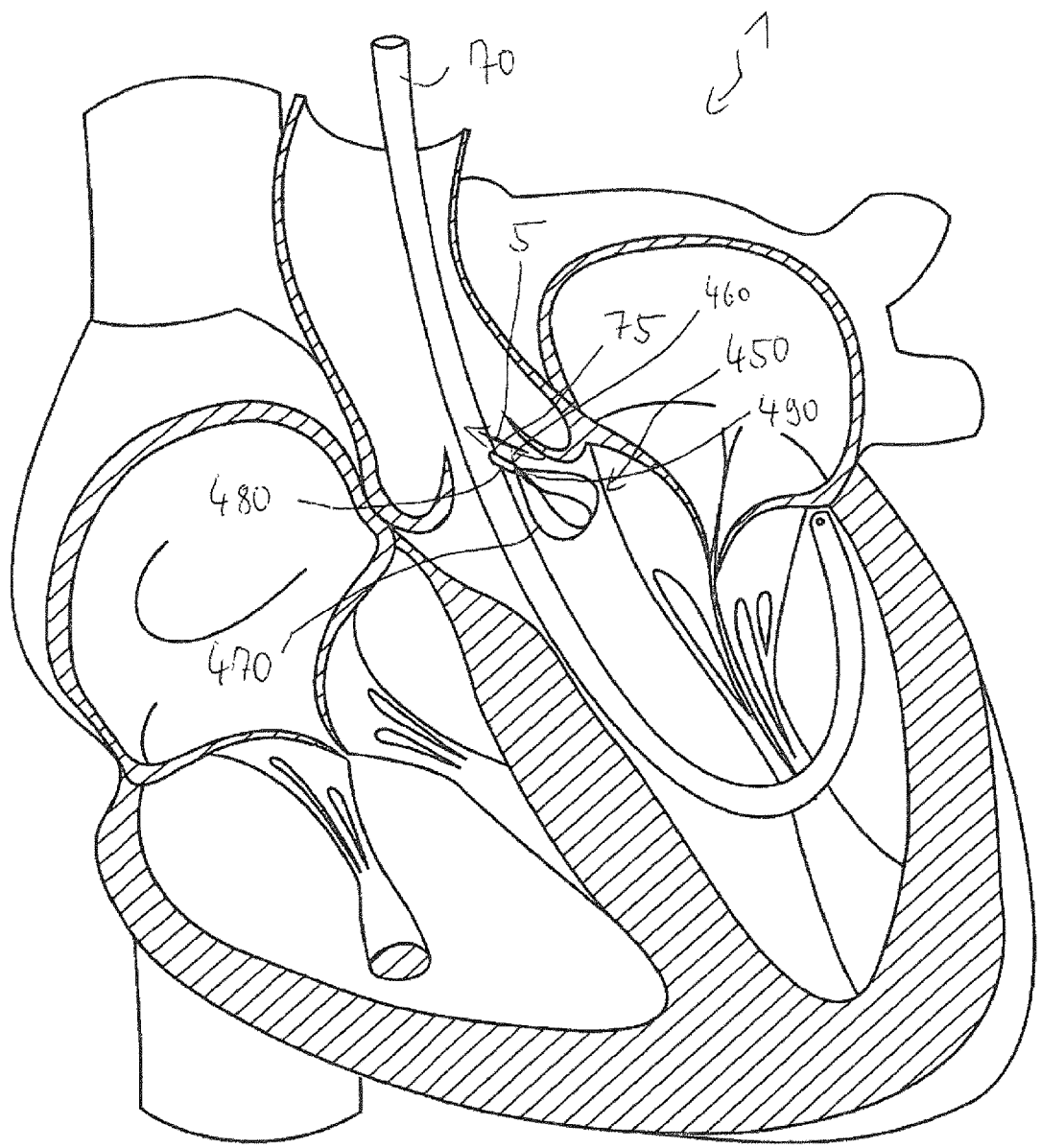

As shown in FIG. 15*b*, the catching mechanism 450 (here comprising catching basket 470 as a catching device) may be forwarded and exposed from the primary catheter 70, e.g. using the controller 460 (here implemented as a control wire 490 and control catheter 480 that is is (partially) sheathed in primary catheter 70) so that the catching basket 470 assumes its unfolded/uncompressed state, as indicated by arrow 5 in FIG. 15*b*.

Figure 15C:
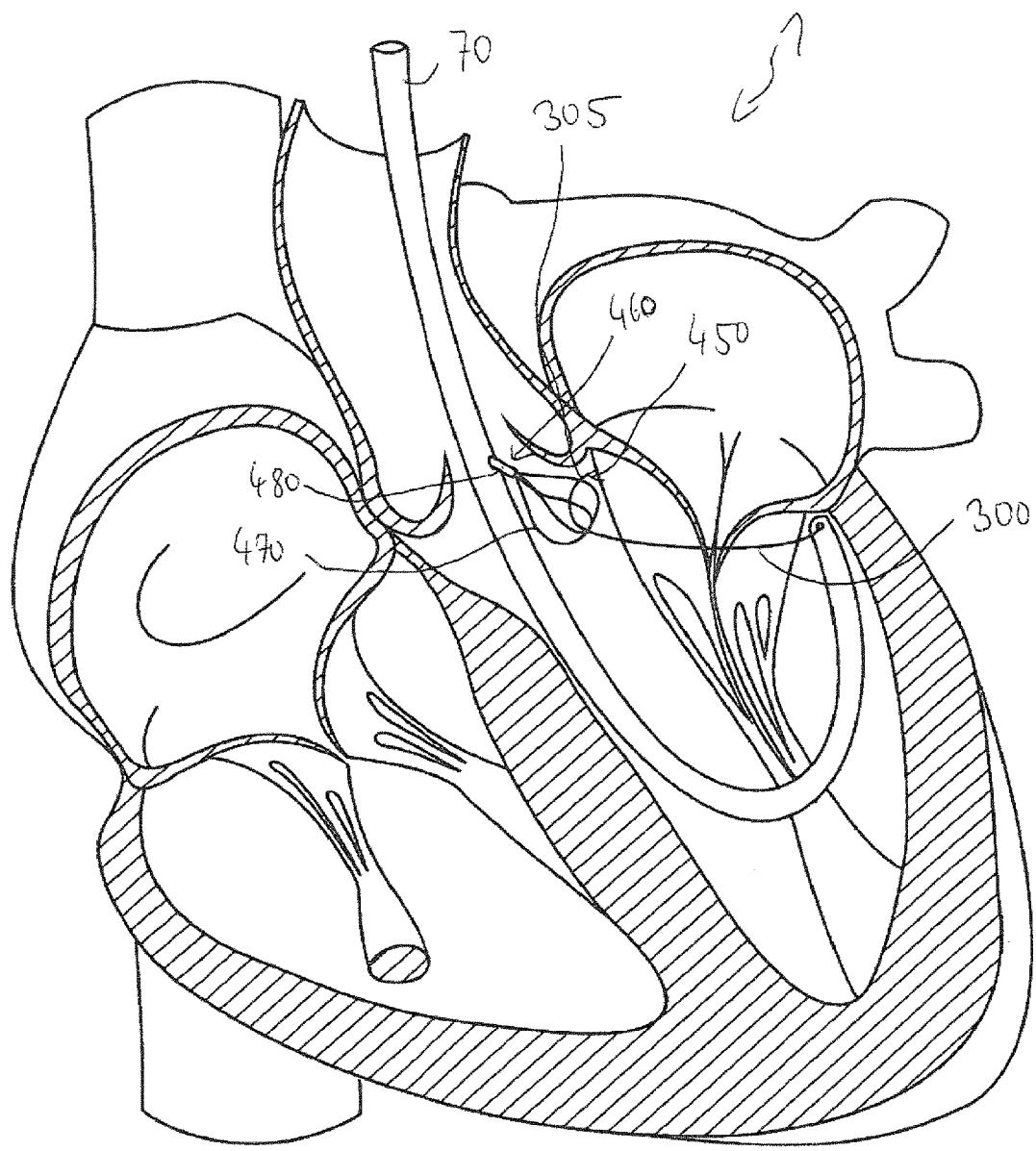

As shown in FIG. 15*c*, the distal end 305 of wire 300 may be caught by catching mechanism 450. In order to be caught, the distal end 305 may e.g. be forwarded so that it is extending through the catching mechanism 450 when it is implemented as a catching basket 470 or may e.g. be magnetically drawn to the catching device when it comprises a magnetic component. In this respect, wire 300 may be forwarded to extend (at least partially) around tissue structure 10 and to get caught by catching mechanism 450 for example using a secondary catheter 120, 130 and/or tertiary catheter 200, 210 substantially as described above, or by other means. Catching basket 470 may optionally also be made from a magnetic material and/or may be implemented comprising an electro-magnet in order to further improve catching performance. If secondary and tertiary catheters as described above are used to forward wire 300 so that it extends (at least partially) circumferentially around tissue structure 10, these are retracted back into primary catheter 70 after wire 300 was forwarded and are therefore not visible in FIG. 15*c*.

In addition or as an alternative, the free distal end 305 of wire 300 may be caught by the distal catching component 315 provided with catching wire 310 as described above (see e.g. FIG. 10) after or while or before wire 300 (e.g. distal end 305 thereof), catching component 315 and/or catching wire 310 are caught by catching mechanism 450. Further, also the loop formed by wire 300, that is formed e.g. by catching distal end 305 of wire 300 by using the catching component 315 provided with catching wire 310 and by then retracting the distal end 305 of wire 300 back into primary catheter 70, may be caught by catching mechanism 450 (which results in wire 300 getting caught by catching mechanism 450 (e.g. the catching device thereof).

Figure 15D:
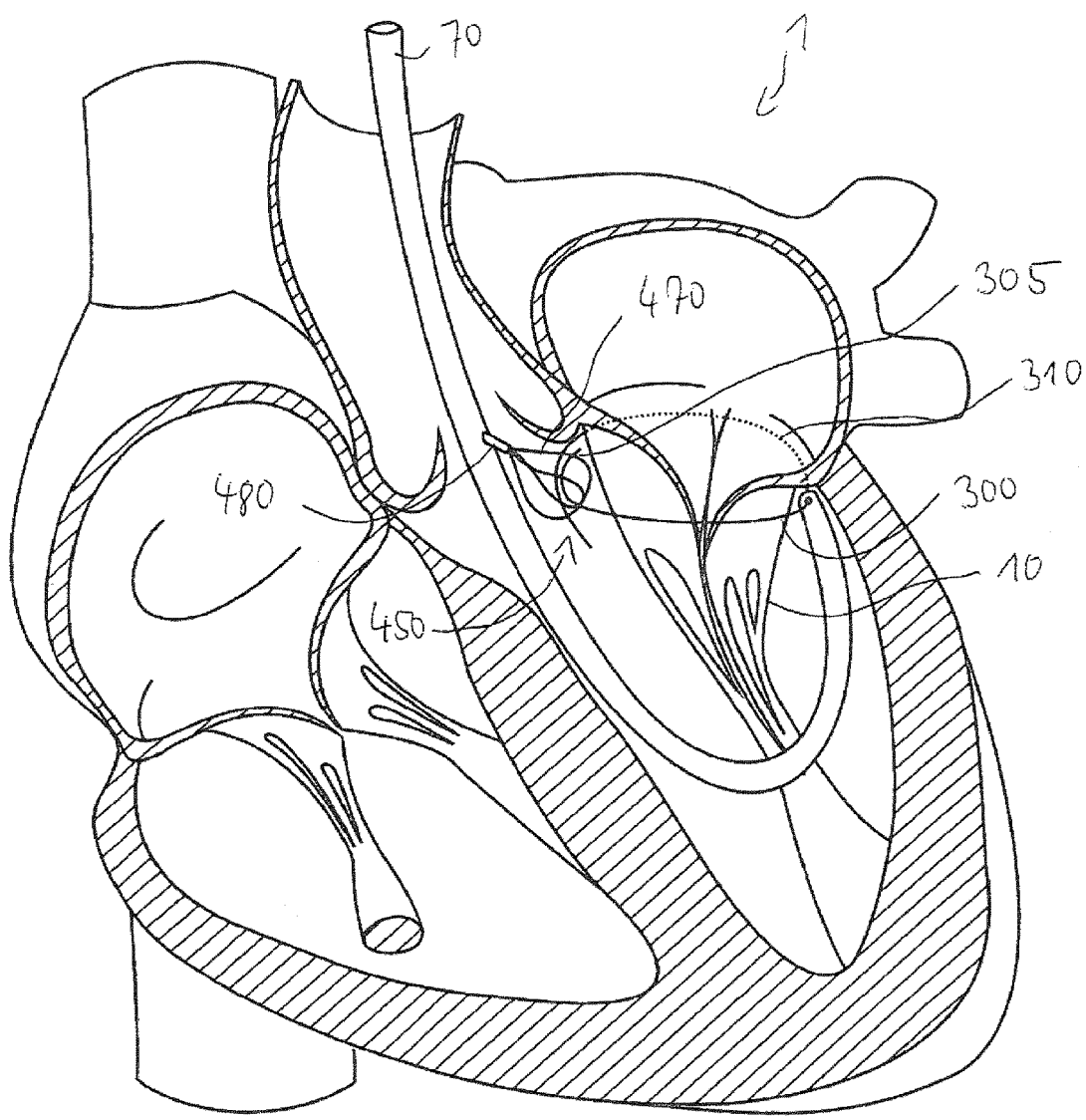

As shown in FIG. 15*d*, the catching/second wire 310 may be forwarded from the distal end portion 100 of primary catheter 70, that is positioned on a side of the circumferential tissue structure 10 that is opposite to the aortic arch 340, in order to extend (at least partially) around tissue structure 10 so that the distal end portion of catching/second wire 310 is caught by the catching mechanism 450, that is positioned oppositely to distal end portion 100 of the primary catheter 70 with respect to circumferential tissue structure 10, using a secondary catheter 120, 130 and/or a tertiary catheter 200, 210 as described above, or by other means. As in FIG. 15*c*, in FIG. 15*d* any secondary catheter 120, 130 or tertiary catheter 200, 210 that nay have been used previously is shown in a state retracted into primary catheter 70 and accordingly not visible in FIG. 15*d*. As further shown in FIG. 15*d*, wire 300 (which may also be designated as first wire 300) and catching/second wire 310 both may be extending from the distal end portion 100 of primary catheter 70 to the catching mechanism 450, wherein both wires 300, 310 may extend on radially opposite sides of tissue structure 10 so that a loop extending (e.g. fully extending) circumferentially around tissue structure 10 is formed and the distal ends of both wires 300, 310 are caught by the catching mechanism 450 (e.g. using a catching device such as the catching basket 470 that is shown in FIG. 15*d*). When the distal ends of wires 300, 310 (and/or catching component 315) are securely caught by catching mechanism 450, the position of the wires 300, 310 (e.g. the loop extending circumferentially around the tissue structure 10) may be selectively changed axially with respect to axis 500, as indicted by arrow 5 in FIG. 15*e*, by moving the to catching mechanism 450 (and hence the caught wire(s) or other elements) relative to the primary catheter 70. Accordingly, the loop formed by wire 300 and/or wire 310 may be precisely positioned with respect to the tissue structure 10 and/or a medical implant such as an artificial heart valve or the like that may e.g. be provided inside the tissue structure 10.

Figure 15E:
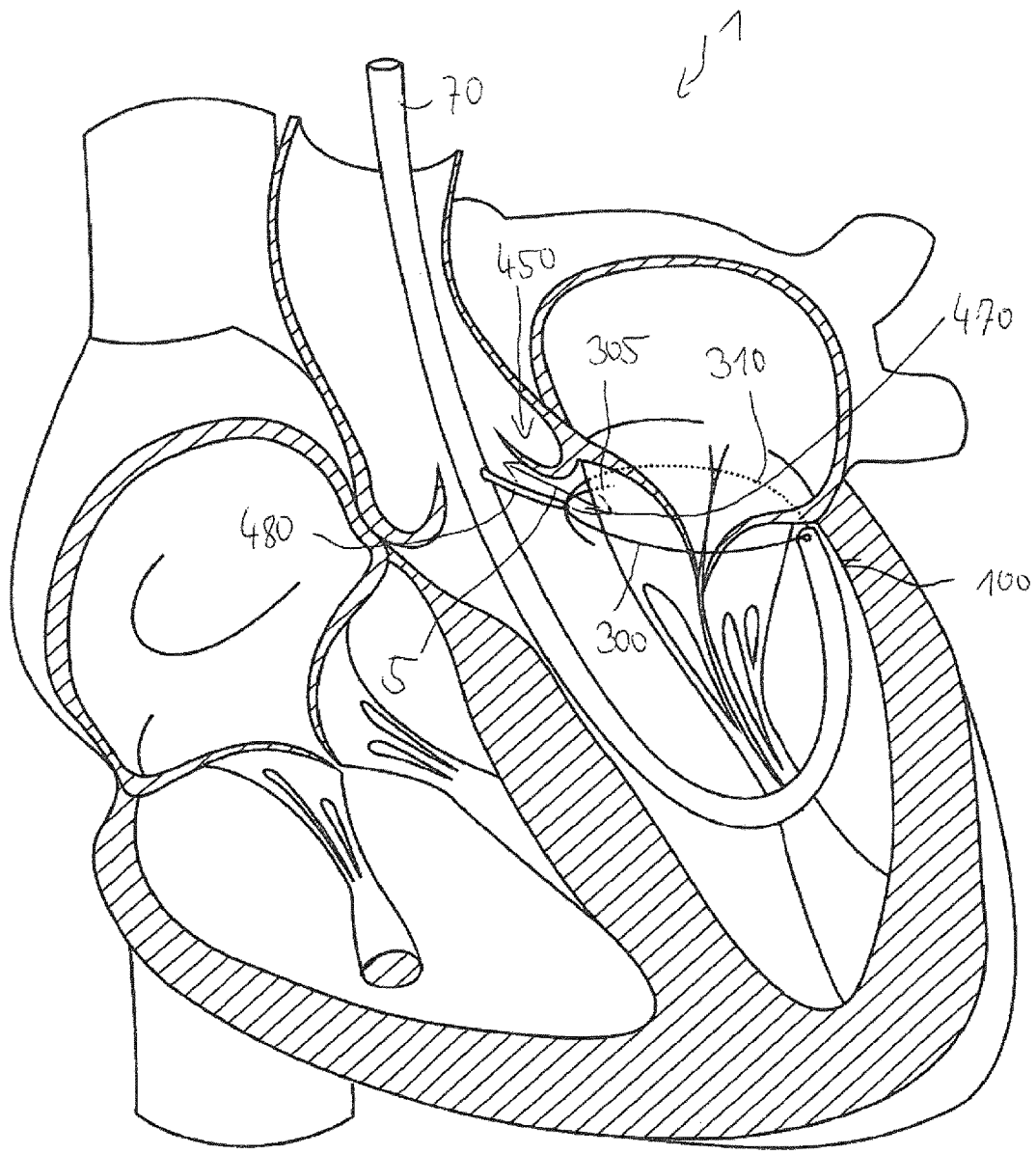

As exemplified in FIG. 15*e*, when a catching basket 470 is used as the catching device of catching mechanism 450, wires 300, 310 and/or catching component 315 may be more securely caught by the catching basket 470 when the catching basket 470 is (at least partially) retracted back into control catheter 480 (e.g. an or the inner lumen thereof), so that wire 300, wire 310 and/or catching component 315 may be securely held by a press fit between the catching basket 470 and the control catheter 480 (e.g. the distal end thereof) and/or may be partially drawn into the inner lumen of control catheter 480 so as to be more securely caught. Then, the position of wire 300, wire 310 and/or catching component 315 may be precisely controlled by moving control catheter 480 relative to primary catheter 70 while keeping the position of control wire 490 constant with respect to control catheter 480.

With respect to e.g. FIGS. 13*a*, 13*b* and 15*a* to 15*e*, the catheter member 1 may assume a shape so that the distal end portion of the primary catheter 70 is located on a side of tissue structure 10 that is substantially radially opposite from the aortic arch 340 when the catheter member 1 is forwarded to the mitral valve 360 via an approach through the aortic arch 340. This shape may be achieved by correspondingly pre-shaping the catheter member 1 or by using the second flexing portion and second flexing mechanism as described herein and/or by pushing a distal end portion 100 of primary catheter 70 in the ventricular chamber 370 substantially along the papillary muscle 60 so that the distal end portion 100 is substantially located radially oppositely to the circumferential tissue structure 10.

According to a further exemplary embodiment, a catheter member 1 for interacting with a circumferential tissue structure 10 is provided, the catheter member 1 comprising: an elongate primary catheter 70 which has an inner lumen 80 and which extends along a longitudinal axis 90 and has a distal end portion 100, first 120 and second 130 elongate secondary catheters each comprising a distal end portion 140, 150 and an inner lumen 160, 170, and each configured to be disposed in the inner lumen 80 of the primary catheter 70 to be moveable relatively thereto and exposable from the distal end portion 100 thereof, and a first flexing mechanism 191 to provide the distal end portion 140, 150 of the first 120 and/or second 130 secondary catheter with a tendency to assume a first secondary bent shape, wherein the distal end portion 140, 150 of one or both of the first and second secondary catheters 120, 130 is configured to be able to be flexed by the first flexing mechanism 191 to form an arm portion 126, 136 substantially transverse to the direction of the longitudinal axis 90 of the primary catheter 70 so as to assume the first secondary bent shape, when being exposed from the distal end portion 100 of the primary catheter 70, and wherein the respective arm portion 126, 136 extends at least 4 mm or at least 5 mm or at least 8 mm or at least 10 mm or at least 12 mm in a direction radial to the longitudinal axis (90) of primary catheter 70 with a free end of the respective arm portion facing away from the longitudinal axis 90 so that the respective aim portion 126, 136, with a lateral outer surface thereof, forms a blunt end face extending transversely to the longitudinal axis 90 of the primary catheter 70 and allowing the blunt end face to frontally contact the tissue structure 10 with the catheter member 1 in a non-penetrating manner.

In said further exemplary embodiment, optionally the first 120 and second 130 secondary catheters may each comprise a secondary alignment portion 127, 137, which is located between the distal 140, 150 and proximal end portions 180, 190 and adjacent to the distal end portion 140, 150 thereof, wherein the catheter member 1 further comprises a second flexing mechanism 192 to provide the secondary alignment portion 127, 137 of the first 120 and/or second 130 secondary catheter with a tendency to assume a second secondary bent shape, wherein the secondary alignment portion 127, 137 of the first 120 and second 130 secondary catheters is configured to be able to be flexed by the second flexing mechanism 192 to assume the second secondary bent shape having a predetermined curvature, optionally with a radius of substantially 30 to 70 mm and optionally describing an angle of 90.degree. to 270.degree., and wherein the first secondary catheter 120 has a longitudinal axis 125 and the second secondary catheter 130 has a longitudinal axis 135, wherein the arm portions 126, 136 of the first 120 and second 130 secondary catheters, respectively, and the distal end portion 100 of the primary catheter 70 are with respect to their respective longitudinal axes 90, 125, 135 extending in the same predetermined plane when the secondary alignment portions 127, 137 of the first 120 and second 130 secondary catheters assume the second secondary bent shape in parallel to each other. Said further exemplary embodiment may also be combined with the subject matter of any or several or all of the claims as attached hereto.

What is claimed is:

1. A catheter member for interacting with a circumferential tissue structure comprising:
    an elongate primary catheter which has at least one inner lumen and which extends along a longitudinal axis and has a distal end portion and a proximal end portion,
    first and second elongate secondary catheters each extending along a longitudinal axis, each comprising a distal end portion and a proximal end portion and an inner lumen, and each comprising a secondary alignment portion, which is located between the distal and proximal end portions and adjacent to the distal end portion, and each positionable in an inner lumen of the primary catheter to be moveable relatively thereto and exposable therefrom,
    a first flexing mechanism to provide the distal end portion of the first and/or second secondary catheter with a tendency to assume a first secondary bent shape, and
    a second flexing mechanism to provide the secondary alignment portion of the first and/or second secondary catheter with a tendency to assume a second secondary bent shape,
    wherein
    the distal end portion of at least one of the first and second secondary catheters is configured to be able to be flexed by the first flexing mechanism to form an arm portion substantially transverse to the direction of the longitudinal axis of the primary catheter so as to assume the first secondary bent shape, when being exposed from the distal end portion of the primary catheter,
    the secondary alignment portion of at least one of the first and second secondary catheters is configured to be able to be flexed by the second flexing mechanism to assume the second secondary bent shape having a predetermined curvature, optionally with a radius of substantially 30 to 70 mm and optionally describing an angle of 90° to 270°,
    the arm portions of the first and second secondary catheters, respectively, extend in different directions to each other when the secondary alignment portions of the first and second secondary catheters assume the second secondary bent shape in parallel to each other,
    the primary catheter is provided with a radial opening having a distance to the distal end portion and the proximal end portion thereof, and
    the catheter member further comprises a catching device configured to be at least partially sheathed in the inner lumen of the primary catheter member to be moveable thereto and to be at least partially exposable from the primary catheter via the opening.

2. The catheter member according to claim 1, further comprising first and/or second elongate tertiary catheters to be guided by the first and/or second secondary catheters, respectively, each extending along a longitudinal axis and each comprising a distal end portion and a proximal end portion and each to be moveable relatively to the first and/or second secondary catheters, respectively, and exposable from the distal end portions thereof.

3. The catheter member according to claim 2, wherein the first and/or second tertiary catheters each has a first and/or a second tertiary alignment portion between the respective distal and proximal end portions thereof, each with a shape-memory structure providing the first and/or the second tertiary alignment portions with a tendency to assume a first and/or a second tertiary bent shape, respectively, corresponding to the first and/or to the second secondary bent shape, respectively.

4. The catheter member according to claim 3, wherein the shape-memory structure of the distal end portions of the first and the second tertiary catheters is such that, when, the first and/or the second tertiary alignment portion of the first and the second tertiary catheters are located so as to mate with the distal end portions and/or the secondary alignment portions of the first and second secondary catheter, assuming their respective first and/or second bent shape, respectively, the distal end portions of the first and the second tertiary catheters are provided with a tendency to assume bow shapes extending oppositely towards each other so as to form a loop-shape.

5. The catheter member according to claim 4, wherein, when the first and second distal end portions of the first and second tertiary catheter are exposed from the distal end portion of the first and second secondary catheters, the distal end portions of the first and second tertiary catheters each substantially extend in a substantially same plane that is transverse to the longitudinal axis of the primary catheter.

6. The catheter member according to claim 3, wherein, when the first and/or the second tertiary alignment portion of the first and the second tertiary catheters are located so as to mate with the distal end portions and/or the secondary alignment portions of the first and second secondary catheter, assuming their respective first and/or second bent shape, respectively, the distal end portions of the first and the second tertiary catheters are fully operatively exposed from the distal end portions of the first and second secondary catheters.

7. The catheter member according to claim 3, wherein the shape-memory structure is provided by material elasticity.

8. The catheter member according to claim 2, wherein the distal end portions of the first and the second tertiary catheters comprise a shape-memory structure providing them with a tendency to assume a respective bow shape when being exposed from the distal end portion of the first and second secondary catheters, respectively.

9. The catheter member according to claim 2, wherein
the first and second tertiary catheters each comprises an inner lumen,
a wire having a free distal end is provided in the inner lumen of the first tertiary catheter and a catching wire optionally with a catching component on a distal end thereof is provided in the inner lumen of the second tertiary catheter, and
both the wire and the catching wire are provided to be movable relative to their respective tertiary catheter and exposable from and retractable into a distal end portion thereof, so that the free distal end of the wire can be caught with the catching component so as to form a loop.

10. The catheter member according to claim 9, wherein the catching component is a catching basket and/or a lasso and/or a snare.

11. The catheter member according to claim 9, wherein
the wire and/or the catching wire has a shape memory structure giving it a tendency to assume a bow shape,
a strength of the shape memory structure of the wire and/or the catching wire is higher than a strength of a shape memory structure of the distal end portion of the first and/or second tertiary catheter so that the wire and/or catching wire unwinds a coil shape of the distal end portion of the first and/or second tertiary catheter when forwarded through the first and/or second tertiary catheter so that the distal end portion of the first and/or second tertiary catheter assumes the bow-shape of the wire and/or catching wire, and
optionally the catching wire does not comprise a catching component.

12. The catheter member according to claim 9, wherein the catching device is configured to catch a respective free distal end of the wire and/or the catching wire and/or to catch the loop, optionally when the first and/or second secondary catheter has assumed the second secondary bent shape, and to move said caught distal end or distal ends or loop with respect to the primary catheter.

13. The catheter member according to claim 12, wherein the catching device is connected to a distal longitudinal end of a control wire, and a control catheter having an inner lumen that is provided in the primary catheter to be moveable relatively thereto and to be exposable via the opening,
the control wire and the catching device are configured to be at least partially sheathed in the inner lumen of control catheter to be relatively moveable thereto, and
the catching device is forwardable from and retractable into the inner lumen of the control catheter to be exposed or sheathed, respectively.

14. The catheter member according to claim 13, wherein the catching device comprises a catching basket, a magnetic component, a hook, a snare and/or a lasso.

15. The catheter member according to claim 2, wherein one or both of the first and second tertiary catheters are received in the inner lumen of the first and second secondary catheter, respectively, so as to be guided by them.

16. The catheter member according to claim 2, wherein
the first and/or second tertiary catheter comprises an inner lumen, and
one or both of the first and second secondary catheter, respectively, are received in the inner lumen of the first and/or second tertiary catheter, respectively, so that the first and/or second tertiary catheter are guided by the first and/or second secondary catheter, respectively.

17. The catheter member according to claim 2, wherein
the distal end portion of the first and/or second tertiary catheter has a shape memory structure giving it a tendency to assume a coil shape having a plurality of windings, at least when the distal end portion of the first and/or second tertiary catheter is exposed from the distal end portion of the first and/or second secondary catheter, respectively, and
optionally the coil shape of the distal end portion of the first and/or second tertiary catheter is diametrically compressed when sheathed in the inner lumen of the first and/or second secondary catheter.

18. The catheter member according to claim 17, wherein
a wire having a free distal end is provided in the inner lumen of the first tertiary catheter and/or a catching wire optionally with a catching component on a distal end thereof is provided in the inner lumen of the second tertiary catheter,
the wire and/or the catching wire has a shape memory structure giving it a tendency to assume a bow shape, and
a strength of the shape memory structure of the wire and/or the catching wire is higher than a strength of the shape memory structure of the distal end portion of the first and/or second tertiary catheter so that the wire and/or catching wire unwinds the coil shape of the distal end portion of the first and/or second tertiary catheter when forwarded through the first and/or second tertiary catheter so that the distal end portion of the first and/or second tertiary catheter assumes the bow-shape of the wire and/or catching wire.

19. The catheter member according to claim 1, wherein the curvature of the second secondary bent shape is configured to mate the curvature of an aortic arch of a mammal heart and the circumferential tissue structure is part or all of the mitral valve apparatus.

20. The catheter member according to claim 1, wherein the curvature of the second secondary bent shape is configured to mate the curvature of a connection channel from the superior vena cava to the pulmonary artery of a mammal heart and the circumferential tissue structure is part or all of the tricuspid valve apparatus.

21. The catheter member according to claim 1, wherein the primary catheter further comprises a front body tube moveably disposed in its inner lumen, and the front body tube comprises a blunt front body on its distal end portion that is configured to selectively open and close the distal, end portion of the primary catheter by movement of the front body tube in a distal or proximal direction, respectively, of the primary catheter.

22. The catheter member according to claim 1, wherein the first flexing mechanism and/or the second flexing mechanism comprise a shape-memory structure, a flexing structure having an atraumatic nose cone and/or threads attached to the distal end portion of the first and/or second secondary catheter and/or a hinge member rotatably connecting first and second secondary catheters and an inflatable member that is provided between the first and second secondary catheters, and/or at least one link member and at least two joint members interconnecting first and second secondary catheters, and/or at least two link members and at least three joint members and a longitudinal operation member that is movable in a longitudinal direction of primary catheter, the first secondary catheter is connected to a first link member via a first joint member, the second secondary catheter is connected to a second link member via a second joint member and the first and second link members are connected via a third joint member, and the third joint member or the first link member or the second link member is connected to the operation member to be movable in the longitudinal direction of primary catheter.

23. The catheter member according to claim 1, wherein the respective arm portion extends at least 5 mm or at least 8 mm or at least 10 mm or at least 12 mm in a direction radial to the longitudinal axis of primary catheter with a free end of the respective arm portion facing away from the longitudinal axis so that the respective arm forms a blunt end face extending transversely to the longitudinal axis of the primary catheter and allowing to frontally contact the tissue structure with the catheter member in a non-penetrating manner.

24. The catheter member according to claim 1 in combination with an implant, wherein one or both of the first and second tertiary catheters is/are configured so as to deliver the implant to the circumferential tissue structure.

* * * * *